US008586618B2

(12) United States Patent
Kumar et al.

(10) Patent No.: US 8,586,618 B2
(45) Date of Patent: Nov. 19, 2013

(54) FURANONE COMPOUNDS AND LACTAM ANALOGUES THEREOF

(75) Inventors: Naresh Kumar, New South Wales (AU); George Iskander, New South Wales (AU)

(73) Assignee: Biosignal Limited, New South Wales (AU)

( * ) Notice: Subject to any disclaimer, the term of this patent is extended or adjusted under 35 U.S.C. 154(b) by 104 days.

(21) Appl. No.: 12/311,473

(22) PCT Filed: Oct. 8, 2007

(86) PCT No.: PCT/AU2007/001523
§ 371 (c)(1),
(2), (4) Date: Jun. 3, 2009

(87) PCT Pub. No.: WO2008/040097
PCT Pub. Date: Apr. 10, 2008

(65) Prior Publication Data
US 2010/0035948 A1 Feb. 11, 2010

(30) Foreign Application Priority Data

Oct. 6, 2006 (AU) ................................ 2006905579

(51) Int. Cl.
*A01N 43/36* (2006.01)
*A61K 31/40* (2006.01)
(52) U.S. Cl.
USPC .......................................... 514/408; 514/423
(58) Field of Classification Search
USPC ........................................ 514/378, 408, 423
See application file for complete search history.

(56) References Cited

U.S. PATENT DOCUMENTS

| 4,260,598 A | 4/1981 | Barth |
| 4,968,817 A | 11/1990 | Brima |

FOREIGN PATENT DOCUMENTS

| DE | 25 38 771 | 3/1977 |
| DE | 25 38 771 A | 3/1977 |
| EP | 0 418 020 A2 | 3/1991 |
| WO | WO 00/37477 | 6/2000 |
| WO | WO 00/37477 A1 | 6/2000 |
| WO | WO 02/47681 A1 | 6/2002 |
| WO | WO 02/102370 A1 | 12/2002 |

OTHER PUBLICATIONS

Boiadjiev et al. ("N21, N22-Carbonyl-bridged Biliverdin. Red-blue Color Change Effected by Conformation" J. Heterocyclic Chem., 2005, 42, 161-164).*
Kinoshita et al. ("A New and Convenient Wittig-type Reaction for the Preparation of Pyrromethenone Derivative" Chemistry Letters, 1993, 8, 1441-1442).*
Brower et al. ("Fluorophenyl Bilirubins: Synthesis and Sterochemistry" Monatscheffe für Chemie, 132, 2001, 1527-1546).*
STN File Registry, entered STN: Jun. 1, 2005; Registration No. 851458-15-6.

STN File CA, Abstract 145:124757 & Margaros, I., et al; *Tetrahedron* (2006), 62(22), pp. 5308-5317, Abstract & CAS Registration No. 136762-94-2.
STN File CA, Abstract 143:440145 & Kar, A., et al; *Synthesis* (2005), 14 pp. 2284-2286, Abstract & CAS Registration No. 216227-78-0 & 136762-97-5.
STN File CA, Abstract 141:379751 & Bang, S-C., et al; *Archives of Pharmaceutical Research* (2004), 27(5), pp. 485-494, Abstract & CAS Registration No. 782480-30-2, 782480-29-9, 13327-36-1, 782479-91-8, 782479-92-9, 782479-93-0, 782479-95-2, 782479-96-3, 782480-05-1, 782480-08-4, 782480-11-9, 782480-12-0, 782480-15-3, 782480-16-4, 782480-19-7, 782480-20-0, 782480-22-2, 782480-09-5, 782480-10-8, 782480-13-1, 782480-14-2, 782480-17-5, 782480-18-6, 97323-38-1, 123393-94-2, 123394-12-7, 782480-00-6, 782480-01-7, 782480-02-8, 782480-03-9, 782480-07-3, 782480-21-1, 35304-77-9, 97323-25-6, 97323-30-3, 97323-32-5, 214049-81-7, 782479-94-1, 782479-97-4, 782479-98-5, 782480-04-0 & 782480-06-2.
STN File CA, Abstract 140: 303472 & Sorg, A., et al; *Synlett* (2004), 2, pp. 321-325, Abstract & CAS Registration No. 676556-29-9, 35304-86-0 & 35304-87-1.
STN File CA, Abstract 140:181270 & Piper, S., et al; *ARKIVOC* (Gainsville, FL, United States) (2003), 1, pp. 86-91, Abstract & CAS Registration No. 35304-77-9, 35304-78-0, 35304-86-0, 35304-87-1, 97323-27-8, 123393-94-2, 123394-12-7 & 657404-94-9.
STN File CA, Abstract 139:395775 & Rousset, S., et al; *Tetrahedron Letters* (2003), 44(41), pp. 7633-7636, Abstract & CAS Registration No. 35304-86-0.
STN File CA, Abstract 138:170020 & Wu, J., et al; *Journal of Organic Chemistry* (2003), 68(2), pp. 670-673, Abstract & CAS Registration No. 497824-88-1 & 497824-89-2.
STN File CA, Abstract 137:369913 & Sundar, N., et al; *Synthetic Communications* (2002), 32(12), pp. 1881-1886, Abstract & CAS Registration No. 2209-42-9, 2209-43-0, 5705-62-4, 35304-77-9, 35304-78-0, 35304-91-7, 475232-68-9 & 475232-69-0.
STN File, CA Abstract 131:257352 & Prim, D., et al; *Journal of the Chemical Society, Perkin Transactions 2, Physical Organic Chemistry* (1999) 6, pp. 1175-1180, Abstract & CAS Registration No. 244625-15-8 & 244625-17-0.

(Continued)

*Primary Examiner* — Yong Chong
(74) *Attorney, Agent, or Firm* — Nixon & Vanderhye

(57) ABSTRACT

The present invention provides a compound of formula I and a compound of formula II, methods of use and formulations thereof.

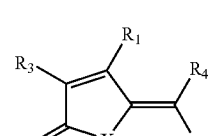

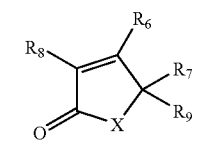

10 Claims, No Drawings

(56) References Cited

OTHER PUBLICATIONS

STN File CA, Abstract 129:275794 & Pohmakotr, M., et al; *Tetrahedron* (1998), 54(37), pp. 11297-11304, Abstract & CAS Registration No. 35304-77-9, 35304-86-0, 214049-79-3, 214049-80-6 & 214049-81-7.

STN File CA, Abstract 126:250856 & Kaigorodova, E.A., et al; *Izvestiya Vysshikh Uchebnykh Zavedenti Khimiya I Khimicheskaya Tekhanologiya* (1996) 39(4-5) pp. 176-179, Abstract & CAS Registration No. 87643-16-1, 188577-00-6 & 188577-02-8.

STN File CA, Abstract 126:185925 & Kotora, M., et al; *Synthesis* (1997), 1, pp. 121-128, Abstract & CAS Registration No. 136763-03-6, 35304-86-0, 136762-95-3, 136763-01-4, 136763-04-7, 136781-96-9 & 187407-41-6.

STN File CA, Abstract 111:194478 & Sorotskaya, L.N., et al; *Zhurnal Organicheskoi Khimii* (1989), 25(1), pp. 175-182, Abstract & CAS Registration No. 2209-42-9, 2209-43-0, 35304-77-9, 35304-78-0, 35304-86-0, 35304-87-1, 123393-94-2, 123393-95-3, 123393-96-4, 123393-97-5, 123394-12-7, 123394-13-8, 123394-14-9, 123394-15-0, 123394-16-1 & 123427-28-1.

STN File CA, Abstract 106:196171 & Stachel, H.D., et al; *Zeitschrift fuer Naturforschungt Teil B: Anorganische Chemie, Organische Chemie* (1986), 41B(5), pp. 640-644, Abstract & CAS Registration No. 105886-78-0 & 108045-36-9.

STN File CA, Abstract 106:18291 & Ribo, J.M., et al; *Monatschefie fuer Chemie* (1986), 117(2), pp. 185-200, Abstract & CAS Registration No. 105886-78-0 & 105886-83-7.

STN File CA, Abstract 104:109384 & Chellar, N.S., et al; *Khimiya I Khim. Tekhnol., Erevan* (1983), 2, pp. 97-101, Abstract & CAS Registration No. 95412-20-7, 95412-22-9 & 100586-93-4.

STN File CA, Abstract 103:53889 & Reisch, J., et al; *Archiv der Pharmazie* (1985), 318(5), pp. 459-464, Abstract & CAS Registration No. 35304-77-9, 35304-86-0, 97323-25-6, 97323-26-7, 97323-27-8, 97323-28-9, 97323-29-0, 97323-30-3, 97323-31-4, 97323-32-5, 97323-33-6, 97323-34-7, 97323-35-8, 97323-36-9, 97323-37-0, 97323-38-1, 97323-39-2 & 97323-40-5.

STN File CA, Abstract 99:175497 & Reisch, J, et al; *Monatshefte fuer Chemie* (1983), 114(5), pp. 635-637, Abstract & CAS Registration No. 5705-61-3, 87643-15-0 & 87643-16-1.

STN File CA, Abstract 96:122537 & Asaoka, M., et al; *Tetrahedron Letters* (1981), 22(43), pp. 4269-4270, Abstract & CAS Registration No. 2209-42-9, 2209-43-0, 5705-62-4, 35304-86-0, 35304-87-1 & 35304-91-7.

STN File CA, Abstract 76:46022 & Yamada, K., et al; *Tetrahedron* (1971), 27(22), pp. 5445-5451, Abstract & CAS Registration No. 5705-62-4, 24948-12-7, 24948-13-8, 35304-77-9, 35304-78-0, 35304-86-0, 35304-87-1 & 35304-91-7.

STN File CA Abstract 130:24885 & Boukouvalas, J., et al; *Tetrahedron Letters* (1998), 39(42), pp. 7665-7668, Abstract & CAS Registration No. 56634-50-5, 3516-65-2, 1575-47-9, 87979-60-0, 144465-13-4, 144465-15-6, 179123-02-5 & 216227-85-9.

STN File CA, Abstract 116:200938 & Anselmi, C., *Chemtech* (1992), 22(2), pp. 99-104, Abstract & CAS Registration No. 4031-15-6.

STN File CA, Abstract 146:4425 & Manzanaro, S., et al; *Journal of Natural Products* (2006), 69(10), pp. 1485-1487, Abstract & CAS Registration No. 136762-94-2, 136762-95-3 & 287964-86-7.

STN File CA, Abstract 146:500812 & Duchene, A., et al; *Synthesis* (2007), 4, pp. 597-607, Abstract & CAS Registration No. 35304-87-1, 35304-86-0, 2209-43-0 & 936255-07-1.

STN File CA, Abstract 146:462077 & Boukouvalas, J., et al; *Synlett* (2007), 2, pp. 219-222, Abstract & CAS Registration No. 676556-29-9, 935467-31-5, 935467-32-6, 5705-62-4, 35304-77-9 & 35304-86-0.

Australian Patent Examination Report No. 1, Patent Application No. 2007304839, date of issue May 27, 2013 (5 pgs).

Chemical Library, 851458-15-6 Registry, 2 (5H)—Furanone, 5-[(3,4-dichlorophenyl)methylene)-3,4-di-2-thienyl-; CHEMCATS, 2 pgs (2005).

Margaros, I, et al; "The power of singlet oxygen chemistry in biomimetic syntheses"; *Tetrahedron*, vol. 62, pp. 5308-5317 (2006).

Kar, A., et al; "Synthesis 2005", vol. 14, pp. 2284-2286; Div. Org. Chem., Natl Chem. Lab., Pune 411 008, India; Eng., 1 pg (2006).

Bang, S.-C., et al; "5-Arylidene-2(5H)-Furanone Derivatives: Synthesis and Structure-Activity Relationship for Cytoxicity"; *Arch Pharm Res*, vol. 27, No. 5, pp. 485-494 (2004).

Accession No. 140:303472, Sorg, A., et al; "A novel access to γ-alkylidenebutenolides: Sequential Stille couplings of dibromomethylenebutenolides"; (2004).

Piper, S., et al; "γ-Regioselectivity of (furan-2-yloxy)-trimethylsilane towards iminium salts: synthesis of γ-arylidenebutenolides"; *ARKAT USA, Inc.*, vol. 1, pp. 86-92 (2003).

Rousset, S., et al; "Regio- and stereoselective preparation of γ-alkylidenebutenolides or α-pyrones using a Stille reaction and palladium-catalysed oxacyclisation sequence"; *Teradedron Letters*, vol. 44, pp. 7633-7636 (2003).

Wu, J., et al; "Palladium-Catalyzed Cross-Coupling Reactions of 4-Tosyl-2(5H)-furanone with Boronic Acids: A Facile and Efficient Route to Generate 4-Substituted 2(5H)-Furanones"; *J. Org. Chem.*, vol. 68, pp. 670-673 (2003).

Accession No. 137:369913, Sundar, N., et al; "Zoelite mediated stereoselective synthesis of γ-alkylidenebutenolides"; (2002).

Prim, D., et al; "Synthesis and stereochemistry of β-aryl-β-haloacroleins: useful intermediates for the preparation of (Z) (E)-2-en-4-yne-carbaldehydes and for the synthesis of rubrolides"; *J. Chem.. Soc., Perkin Trans.*, vol. 2, pp. 1175-1180 (1999).

Accession No. 129:275794, Pohmakotr, M., et al; "γ-Regioselectivity of lithiated 2-buten-4-olide towards aromatic aldehydes: a sample of synthesis of γ-arylidenebutenolides"; (1998).

Accession No. 126:250856, Kaigorodova, E.A., et al; "Electronic spectral characteristics of condensation products of 2(5H)-furanone and furo[3,4-c]pyridinedione-3,4 wkth heteroaromatic aldehydes"; (1996).

Accession No. 126:185925, Kotora, M., et al; "Highly efficient and selective procedures for the synthesis of .gamma. alkylidenebutenolides via palladium-catalyzed ene-yne coupling and palladium- or silver-catalyzed lactonization of (Z)-2-en-4-ynoic acids. Synthesis os rubrolides A, C, D, and E"; (1997).

Accession No. 111:194478, Sorotskaya, L.N., et al; "Butanolides and butenolides. IV. 4-Arylidene- or 4-heteroarylidene-2-butenolides"; (1989).

Stachel, H-D., et al; "Synthese von 5-Alkyliden-3-pyrrolin-2-onen"; *Zeitschrift Fuer Naturforschung*, pp. 640-644 (1986).

Ribo, J. M., et al; "Reactivity of Pyrrole Pigments. Parts VII[1] Autoxidation of Model Compounds for 5(2H)-Dipyrrylmethanones and 3,4-Dihydro-5(1H)-Pyrromethenones"; *Montshefte für Chemie*; vol. 117, pp. 185-200 (1986).

Accession No. 104:109384, Chellar, N.S., et al; "Condensation of p-substituted 3-aryl-2-butenolides with aromatic and heterocyclic aldehydes" (1985).

Reisch, J., et al; "Ein einstufiges Verfahren zur Darstellung von γ-Yliden-α,β-butenoliden"; *Arch. Pharm.* (Weinheim), vol. 318, pp. 459-464 (1985).

Accession No. 99:175497, Reisch, J., et al; "A simple synthesis of natural products with furan-2(5H)-one structure" (1983).

Asaoka, M., et al; "Synthesis of 4-ylidenebutenolides from 2-trimethylsiloxyfuran"; *Tetrahedron Letters*, vol. 22, No. 43, pp. 4269-4270 (1981).

Accession No. 76:46022, Yamada, K., et al; "Convenient method for the preparation of γ-arylidene-α,β-unsaturated γ-lactones. Application to the synthesis of the thiopene lactone obtained from Chamaemelum nobile"; (1971).

Boukouvalas, J., et al; "Facile Access to 4-Aryl-2(5H)-furanones by Suzuki Cross Coupling: Efficient Synthesis of Rubrolides C and E"; *Tetrahedron Letters*, vol. 39, pp. 7665-7668 (1998).

Anselmi, C., "Staying on the surface"; *Chemtech*, vol. 22, No. 2, pp. 99-104 (1992).

Kinoshita, H., et al; "A New and Convenient Wittig-type Reaction for the Preparation of Pyrromethenone Derivative"; *Chemistry Letters*, pp. 1441-1442 (1993).

\* cited by examiner

FURANONE COMPOUNDS AND LACTAM ANALOGUES THEREOF

This application is the U.S. National Phase of International Application PCT/AU2007/001523, filed Oct. 8, 2007, which designated the U.S. PCT/AU2007/001523 claims priority to Australian Application No. 2006905579, filed Oct. 6, 2006. The entire content of these applications are incorporated herein by reference.

FIELD OF THE INVENTION

The present invention relates to furanone and lactam derivatives which have antibacterial properties, methods for their synthesis and their uses.

BACKGROUND OF THE INVENTION

Certain furanone compounds and lactam analogues of furanone compounds have been shown to have antibacterial properties and are described, for instance, in WO 99/54323 and WO 2004/016588.

The present inventors have found new synthetic approaches which allow them to access novel classes of furanone compounds and lactam analogues thereof. These compounds have antibacterial properties and have been shown to have efficacy in the inhibition of biofilms and expression of virulence.

SUMMARY OF THE INVENTION

Accordingly, in a first aspect, the present invention provides a compound of formula I

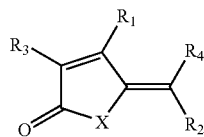

wherein:
X is selected from —O— or —N($R_5$)—;
 wherein $R_5$ is selected from H, alkyl, aryl and arylalkyl;
$R_1$ is selected from H, halo, alkyl, aryl and heteroaryl;
$R_2$ and $R_4$ are each independently selected from hydrogen, aryl and heteroaryl with the proviso that both $R_2$ and $R_4$ cannot be hydrogen; and
$R_3$ is selected from H, alkyl, heteroaryl and aryl.

In a second aspect, the present invention provides a compound of formula II

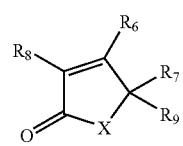

wherein:
X is selected from —O— or —N($R_{10}$)—;
 wherein $R_{10}$ is selected from H, alkyl, aryl and arylalkyl;
$R_6$ is selected from H, halo, alkyl, aryl and heteroaryl;
$R_7$ is selected from H, halo, alkyl, arylalkyl, aryl and heteroaryl;
$R_8$ is selected from H, halo and alkyl; and
$R_9$ is selected from H, halo, alkyl, arylalkyl, aryl and heteroaryl.

In a third aspect, the present provides a method of treating or preventing a microbial infection in a subject, the method comprising administering a compound of formula I or a compound of formula II to the subject.

In a fourth aspect, the present invention provides a method of preventing or inhibiting microbial contamination of a surface, the method comprising administering to the surface a compound of formula I or a compound of formula II.

In a fifth aspect, the present invention provides a formulation comprising a compound of formula I or a compound of formula I.

DETAILED DESCRIPTION OF THE INVENTION

In a first aspect, the present invention provides compound of formula I

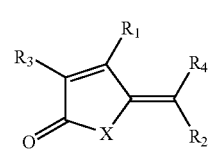

wherein:
X is selected from —O— or —N($R_5$)—;
 wherein $R_5$ is selected from H, alkyl, aryl and arylalkyl;
$R_1$ is selected from H, halo, alkyl, aryl and heteroaryl;
$R_2$ and $R_4$ are each independently selected from hydrogen, aryl and heteroaryl with the proviso that both $R_2$ and $R_4$ cannot be hydrogen; and
$R_3$ is selected from H, alkyl, heteroaryl and aryl.
Preferably, $R_4$ is H.
Preferably $R_3$ is H.
In a preferred embodiment $R_2$ is aryl. Preferably aryl is an optionally substituted phenyl group and even more preferably the optionally substituted phenyl group is substituted with one or more substituents selected from the group consisting of $CF_3$, $OCF_3$, cyano (CN), halo and alkoxyl. It is preferred that halo is F. It is also preferred that alkoxyl is methoxyl.

In another preferred embodiment $R_2$ is heteroaryl. Preferably heteroaryl is a five-membered heteroaromatic ring containing one or more heteroatoms selected from O, N and S. Even more preferably the five-membered heteroaromatic ring is a thiophene.

In yet another preferred embodiment, $R_1$ is aryl. Preferably aryl is an optionally substituted phenyl group, even more preferably the optionally substituted phenyl group is substituted with one or more substituents selected from the group consisting of $CF_3$, $OCF_3$, cyano (CN) and halo. It is preferred that halo is F.

In still another preferred embodiment $R_1$ is heteroaryl. Preferably heteroaryl is a five-membered heteroaromatic ring containing one or more heteroatoms selected from O, N and S. Even more preferably the five-membered heteroaromatic ring is a thiophene.

In yet another preferred embodiment $R_1$ is halo, preferably halo is Br.

In another preferred embodiment, each of $R_1$ and $R_2$ are the same substituent selected from aryl and heteroaryl. Preferably, aryl.

In a preferred embodiment, the present invention provides a compound selected from compounds 13, 17, 18, 19, 20, 21, 22, 23, 24, 25, 28, 29, 30, 31, 32, and 33, as defined in the Examples.

In a second aspect, the present invention provides a compound of formula II

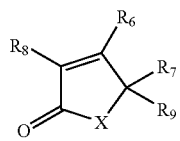

wherein:

X is selected from —O— or —N($R_{10}$)—;

wherein $R_{10}$ is selected from H, alkyl, aryl and arylalkyl;

$R_6$ is selected from H, halo, alkyl, aryl and heteroaryl;

$R_7$ is selected from H, halo, alkyl, arylalkyl, aryl and heteroaryl;

$R_8$ is selected from H, halo and alkyl; and $R_9$ is selected from H, halo, alkyl, arylalkyl, aryl and heteroaryl.

Preferably $R_8$ is H or halo. Preferably halo is Br.

In a preferred embodiment, each of $R_7$ and $R_9$ is H.

In still another preferred embodiment $R_7$ and $R_8$ are each independently selected from H and alkyl.

In another preferred embodiment $R_6$ is aryl. Preferably aryl is an optionally substituted phenyl group. It is preferred that the optionally substituted phenyl group is substituted with one or more substituents selected from the group consisting of $CF_3$, $OCF_3$, cyano (CN) and halo. Preferably halo is F or Br.

In still another preferred embodiment $R_6$ is heteroaryl. Preferably heteroaryl is a five-membered heteroaromatic ring containing one or more heteroatoms selected from O, N and S. Even more preferably the five-membered heteroaromatic ring is selected from the group consisting of thiophene, isoxazole, furan and pyrazole. The five-membered heteroaromatic ring may be substituted with one or more alkyl groups. Preferably the one or more alkyl groups are methyl.

In yet another preferred embodiment $R_6$ is halo, preferably halo is Br.

In a preferred embodiment, the present invention provides a compound selected from compounds 1, 2, 3, 4, 5, 6, 7, 8, 9, 10, 11, 12, 14, 15, 16, 26, 27, 35 and 36 as defined in the Examples.

In a third aspect, the present provides a method of treating or preventing a microbial infection in a subject, the method comprising administering a compound of formula I or a compound of formula II to the subject.

The microbial infection may be a bacterial, protozoal or fungal infection. Preferably, the infection is a bacterial infection.

The compounds of the present invention can act as quorum sensing inhibitors. In particular, the compounds have been shown to inhibit quorum sensing in *Pseudomonas* sp. The compounds therefore find use in any application where the inhibition of quorum sensing is desired. For example, the compounds of the present invention may have use in preventing the establishment of biofilms and expression of virulence by microorganisms through the inhibition of quorum sensing systems and/or other extracellular systems (eg see, International publication No WO 2002/047681, the disclosure of which is incorporated herein in its entirety).

The compounds of the present invention have been shown to inhibit the formation of *Pseudomonas* sp. and *E. coli* biofilms. The formation of biofilms is one instance of quorum sensing. The presence of the quorum sensing pathways (such as those involving homoserine lactones) in a wide range of bacteria indicates that the compounds of the present invention can be used to effectively treat not only *Pseudomonas* sp. and *E. coli* biofilms but also biofilms composed of other bacteria.

The following is a non-exhaustive list of groups of Gram-Negative bacteria that have members which use homoserine lactones for cell-cell communication: anaerobic Gram Negative Straight, Curved and Helical Rods; Bacteroidaceae; The Rickettsias and Chlamydias; Dissimilatory Sulfate—or Sulfur-Reducing Bacteria; the *Mycoplasmas*; The mycobacteria; Budding and/or Appendaged Bacteria; Sheathed Bacteria; Nocardioforms; and *Actinomycetes*, for example. See Bergey's Manual of Systematic Bacteriology, First Ed., John G. Holt, Editor in Chief (1984), incorporated herein by reference.

Further microbial infections that may be treated by the compounds of the present invention include bacterial infections caused by *Staph. aureus, Staph epidermis, Serratia* spp., *Vibrio* spp., and *Strep. pneumonia* and other organisms including the AI2 system; protozoal infections caused by *Acanthamoeba*; and fungal infections caused by *Fusarium* spp.

Preferably, the method of the third aspect may be used to treat or prevent a microbial infection in a subject that is characterised by biofilm formation.

The present invention is suitable for biofilms originating from a single type of organism and for mixed biofilms. By "mixed biofilms" is meant biofilms created by more than one type of microorganism. It is envisioned that mixed biofilms could be created by at least two organisms from the group consisting of bacteria, algae, fungi, and protozoa.

Non-limiting examples of human infections involving biofilms include dental caries, periodontitis, otitis media, muscular skeletal infections, necrotising fascitis, biliary tract infection, urinary tract infection, respiratory tract infection, osteomyelitis, bacterial prostatitis, native valve endocarditis, cystic fibrosis pneumonia, meloidosis, and nosocomial infections such as ICU pneumonia, urinary catheter cystitis, peritoneal dialysis (CAPD) peritonitis, and biliary stent blockage. Biofilm formation can affect sutures, exit sites, arteriovenous sites, scleral buckles, contact lenses, IUDs, endotracheal tubes, Hickman catheters, central venous catheters, mechanical heart valves, vascular grafts, orthopedic devices, penile prostheses. Further applications are described in Costerton J et al, (1999) Vol. 284, Science pp 1318-1322 and Costerton J and Steward, (2001) Battling Biofilms, Scientific American pp 75-81, the disclosures of which are incorporated herein by reference.

Other locations in which biofilms may form include dental plaque which may lead to gum disease and cavities, contact lenses which may lead to eye infections, ears which may lead to chronic infection and lungs which may lead to pneumonia.

The infection may be of a cystic fibrosis sufferer. The infection may be that resulting from a skin infection, burn infection and/or wound infection. The method and composition of the invention may be particularly suitable for the treatment of infection in immuno compromised individuals.

The compounds of the present invention have been shown to be particularly effective in preventing bacterial contamination of surfaces, in particular by preventing the formation of biofilms.

Accordingly, in a fourth aspect, the present invention provides a method of preventing or inhibiting microbial contamination of a surface, the method comprising administering to the surface a compound of formula I or a compound of formula II.

The microbial contamination may be protozoal, fungal or bacterial contamination.

In a preferred form, the microbial contamination is a bacterial contamination. In a more preferred form, the bacterial contamination is a biofilm.

The surface may be any natural or artificial surface. The term "artificial surface" means that the surface is not naturally occurring. In one embodiment, the surface is not an external surface (eg skin) or an internal surface of a human being or animal. In another embodiment, the surface is an external surface or an internal surface of a human being or animal.

Suitable surfaces include the surfaces of articles for which it is desirable to prevent bacterial contamination. These include: medical devices, for example, implantable biomedical devices such as urinary catheters, percutaneous access catheters, stents, orthopaedic implants, bone and dental ceramics and polymers as well as non-implantable devices such as contact lenses, contact lens storage cases, and the like.

The material from which the article is formed can be a metal, a ceramic, a solid synthetic polymer, or a solid natural polymer, for example a solid biopolymer. Examples of useful materials for this invention are titanium, hydroxyapatite, polyethylene (which are useful materials for orthopaedic implants), polyurethanes, organosiloxane polymers, perfluorinated polymers (which are useful materials for instance for catheters, soft tissue augmentation, and blood contacting devices such as heart valves), acrylic hydrogel polymers, HEMA/GMA polymers and silicon/siloxane hydrogel polymers (for instance for contact lens and intraocular lens applications), and the like, and any combination thereof. Further included are resin composites, compomers and resin-modified glass ionomers used in oral care. The surfaces of these materials can be chemically inert or contain reactive functional groups.

Further examples of articles include archival documents, antiques and art, rare and valuable seeds intended for storage (e. g. seed banks of conservation groups), etc in which case the substrate may be paper, material or other natural or synthetic material.

The article may be a shell fish or aquaculture apparatus, for example, that described in WO 1999/005227, the disclosure of which is incorporated herein by reference.

The surface of the article may be any hard surface such as metal, organic and inorganic polymer surface, natural and synthetic elastomers, board, glass, wood, paper, concrete, rock, marble, gypsum and ceramic materials which optionally are coated, eg with paint, enamel etc; or any soft surface such as fibres of any kind (yarns, textiles, vegetable fibres, rock wool, hair etc.); or porous surfaces; skin (human or animal); keratinous materials (nails etc.). The hard surface can be present in process equipment or components of oil and gas infrastructure, deaeraters, a water treatment plant, cooling equipment, a cooling tower, a water treatment plant, a dairy, a food processing plant, a chemical or pharmaceutical process plant. The porous surface can be present in a filter, eg. a membrane filter.

Particular examples of articles whose surfaces may be treated in accordance with the invention include, but are not limited to, toilet bowls, bathtubs, drains, highchairs, counter tops, vegetables, meat processing rooms, butcher shops, food preparation areas, air ducts, air-conditioners, carpets, paper or woven product treatment, nappies (diapers), personal hygiene products (eg sanitary napkins) and washing machines. The compounds may be formulated in the form of a toilet drop-in or spray-on devices for prevention and removal of soil and under rim cleaner for toilets. The compounds of the present invention also have applications in cleaning of Industrial surfaces such as floors, benches, walls and the like and these and other surfaces in medical establishments such as hospitals (eg surfaces in operating theatres), veterinary hospitals, and in mortuaries and funeral parlours.

Further examples of surfaces which may be treated include hard, rigid surfaces such as tanks and tubing, pipes, glazed ceramic, porcelain, glass, metal, wood, chrome, plastic, vinyl and formica or soft flexible surfaces such as shower curtains, upholstery, laundry and carpeting. It is also envisioned that both woven and non woven and porous and non-porous surfaces would be suitable.

The compound may be administered by any suitable means. For instance, the compound may be attached to the surface using the techniques and surfaces described in WO 2004/016588. Examples include providing the compounds of the present invention as part of an oligomer or polymer by, for instance, co-polymerising the compound with other monomers or attaching the compound to the polymer backbone by techniques well known to those in the art.

Methods for the covalent immobilization of organic molecules onto solid surfaces are well known to those skilled in the art. Interfacial reactions leading to the formation of covalent interfacial bonds are derived from well known organic-synthetic reactions. The choice of immobilization reaction depends on both the nature of the substrate material and the chemical composition of the compound of the present invention that is desired for a particular application.

For example, a compound that contains a hydroxyl group in a side chain distal to the ring system, can be linked covalently onto surfaces using epoxide chemistry analogous to the reaction pathway described for the immobilization of polysaccharides onto epoxidated surfaces in Li et al., Surface Modification of Polymeric Biomaterials (B D Ratner and D G Castner, Eds), Plenum Press, NY, 1996 pages 165-173 (the disclosure of which is incorporated herein in its entirety), through isocyanate groups attached to the surface to produce stable urethane linkages through thermal processes, or through carboxylic acid groups or their equivalents, such as acid chlorides, on the surface to produce ester linkages. A compound that contains an aldehyde group can be linked onto surface amine groups using a reductive animation reaction. A compound that contains a carboxylic acid group can be linked onto surface amine groups using carbodiimide chemistry.

Interfacial coupling reactions must of course be selected not only for their ability to achieve the desired covalent linkage but also for avoidance of adverse effects on the furanone compound or furanone compounds to be attached. Particularly, the furanone ring system tends to be labile to alkaline conditions. Such limitations are well known to those skilled in the art. Among the many possible interfacial coupling reactions known in the art, there is sufficient scope for selection of reactions that proceed in a suitable pH range and with furanones substituted with various functional groups in various positions.

Some solid substrate materials possess reactive surface chemical groups that can undergo chemical reactions with a partner group on a compound and thereby form a covalent interfacial linkage directly.

Alternatively, in situ covalent linkage can be made directly through the addition of a doubly functionalised linker molecule to the active surface in the presence of an appropriate compound, or stepwise by sequential addition of doubly functionalised linker molecules and then an appropriate compound. It is not always possible to immobilize furanone compounds directly onto solid substrate materials; in these cases, surface activation or one or more interfacial bonding layers is used to effect covalent immobilization of the compounds.

Surface activation of solid substrate materials can be achieved in a number of ways. Examples are corona discharge treatment or low pressure plasma treatment of polymers. These methods are well known to introduce a variety of functional groups onto polymeric surfaces.

An alternative approach is to provide an interfacial bonding layer interspersed between the solid substrate material or medical device and the compound layer. The application of a thin interfacial bonding layer can be done using methods such as dip coating, spin coating, or plasma polymerization. The chemistry of the bonding layer is selected such that appropriate reactive chemical groups are provided on the surface of this layer, groups that then are accessible for reaction with compound of the invention.

Particularly versatile is the subsequent application of multiple thin interfacial bonding layers; this method can provide a very wide range of desired chemical groups on the surface for the immobilization of a wide range of functionalized furanones and enables usage of compounds optimized for their biological efficacy.

By providing a thin, surface-coated layer of compounds, the optical quality of antibacterial devices of this invention is not reduced, which makes the invention applicable to transparent ophthalmic devices such as contact lenses and intraocular lenses.

The present invention provides thin surface coatings that provide antimicrobial properties and/or antifungal properties to solid materials onto which the coatings have been applied. More particularly, the coatings may be designed to reduce or prevent colonization of biomedical devices by bacteria that cause adverse effects on the health of human users of biomedical devices when such devices are colonized by bacteria.

Alternatively, the compound may be administered in the form of a formulation.

Accordingly, the present invention further provides a formulation comprising a compound of Formula I or a compound of Formula II and a carrier.

Examples of the types of carrier that may be used with the compounds of Formula I and the compounds of Formula II are disclosed in WO 2004/016588.

The formulations may be in any suitable form. The formulation may include a carrier or diluent. The carrier may be liquid or solid. For example, the compositions may be in the form of a solution or suspension of at least one of the compounds in a liquid. The liquid may be an aqueous solvent or a non-aqueous solvent. The liquid may consist of or comprise a one or more organic solvents. The liquid may be an ionic liquid. Particular examples of carrier or diluents include, but are not limited to, water, polyethylene glycol, propylene glycol, cyclodextrin and derivatives thereof.

The composition may be formulated for delivery in an aerosol or powder form.

The composition may include organic or inorganic polymeric substances. For example, the compound of the invention may be admixed with a polymer or bound to, or adsorbed on to, a polymer.

When the composition is to be formulated as a disinfectant or cleaning formulation, the composition may include conventional additives used in such formulations. Non-limiting examples of the physical form of the formulations include powders, solutions, suspensions, dispersions, emulsions and gels.

A compound of the invention may be incorporated into epidermal bandages and lotions. Alternatively, the compounds of the invention may be incorporated into cosmetic formulations, for example, aftershave lotions, skin creams, deodorants and anti-dandruff shampoos.

Compositions of the present invention may be in the form of an aqueous solution or suspension containing a cleaning-effective amount of the active compound described above. The cleaning composition may be in the form of a spray, a dispensable liquid, or a toilet tank drop-in, under-rim product for prevention, removal and cleaning of toilets and other wet or intermittently wet surfaces in domestic or industrial environments.

The compositions of the present invention may additionally comprise a surfactant selected from the group consisting of anionic, non-ionic, amphoteric, biological surfactants and mixtures thereof. Most preferably, the surfactant is sodium dodecyl sulfate.

One or more adjuvant compounds may be added to the cleaning solution of the present invention. They may be selected from one or more of biocides, fungicides, antibiotics, and mixtures thereof to affect planktonics. pH regulators, perfumes, dyes or colorants may also be added. In addition, the adjuvant could be a cell permeabilisation agent such as EDTA or FDS.

By "cleaning-effective" amount of active compound, it is meant an amount of the compound which is necessary to remove at least 10% of bacteria from a biofilm as determined by a reduction in numbers of bacteria within the biofilm when compared with a biofilm not exposed to the active compound.

Preferably, the formulation is a pharmaceutical formulation.

Formulations for pharmaceutical uses may incorporate pharmaceutically acceptable carriers, diluents and excipients known to those skilled in the art. The formulations make be formulated for parenteral or non-parenteral administration. The formulations may be formulated for methods of introduction including, but not limited to, topical, intradermal, intramuscular, intraperitoneal, intravenous, subcutaneous, intranasal, epidural, ophthalmic, and oral routes. They may be formulated for administration by any convenient route, for example by infusion or bolus injection, by absorption through epithelial or mucocutaneous linings (e.g., oral mucosa, rectal and intestinal mucosa, etc.) and may be administered together with other biologically active agents. Administration may be localized or systemic. The formulation may be formulated for intraventricular and intrathecal injection.

Pulmonary administration can also be employed, e.g., by use of an inhaler or nebulizer, and formulation with an aerosolizing agent.

In certain preferred embodiments the formulation further comprises other active agents such as antibiotics and cleaning agents.

In other embodiments of the present invention, the formulation may be formulated as a dentifrice, a mouthwash or a composition for the treatment of dental caries. The composition may be formulated for acne treatment or cleaning and disinfecting contact lenses (eg as a saline solution).

The term "alkyl" is taken to mean both straight chain and branched alkyl groups such as methyl, ethyl, propyl, isopropyl, butyl, isobutyl, sec-butyl, tertiary butyl, and the like. Preferably the alkyl group is a lower alkyl of 1 to 10 carbon atoms, more preferably 1 to 6 carbon atoms.

In certain embodiments, the carbon chain of the alkyl group is interrupted with one or more heteroatoms. For instance, a polyethylene glycol group of the form —$(CH_2CH_2O)_n$H is to be understood to be an alkyl group of such an embodiment.

The term "cycloalkyl" as used herein refers to cyclic hydrocarbon groups. Suitable cycloalkyl groups include but are not limited to cyclopropyl and cyclohexyl.

The term "alkoxy" denotes straight chain or branched alkyloxy, preferably $C_{1-10}$ alkoxy. Examples include methoxy, ethoxy, n-propoxy, isopropoxy and the different butoxy isomers.

The term "alkenyl" includes groups formed from straight chain, branched or mono- or polycyclic alkenes and polyenes. Substituents include mono- or poly-unsaturated alkyl or cycloalkyl groups as previously defined, preferably $C_{2-10}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, or 1,3,5,7-cyclooctatetraenyl.

The term "alkynyl" as used herein, refers to straight chain or branched hydrocarbon groups containing one or more triple bonds. Suitable alkynyl groups include, but are not limited to ethynyl, propynyl, butynyl, pentynyl and hexenyl.

The term "halogen" includes fluorine, chlorine, bromine or iodine, preferably bromine or fluorine.

The term "heteroatoms" denotes O, N, S or Si.

The term "acyl" used either alone or in compound words such as "acyloxy", "acylthio", "acylamino" or diacylamino" denotes an alkanoyl, aroyl, heteroyl, carbamoyl, alkoxycarbonyl, alkanesulfonyl, arysulfonyl, and is preferably a $C_{1-10}$ alkanoyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkanecarbonyl such as cyclopropanecarbonyl cyclobutanecarbonyl, cyclopentanecarbonyl or cyclohexanecarbonyl; alkanesulfonyl, such as methanesulfonyl or ethanesulfonyl; alkoxysulfonyl, such as methoxysulfonyl or ethoxysulfonyl; heterocycloalkanecarbonyl; heterocycloalkanoyl, such as pyrrolidinylacetyl, pyrrolidinylpropanoyl, pyrrolinylacetyl, pyrrolylacetyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; or heterocyclylglyoxyloyl, such as, thiazolidinylglyoxyloyl or pyrrolidinylglyoxyloyl.

The term "aryl" refers to aryl groups having 6 through 10 carbon atoms and includes, for example, phenyl, naphthyl, indenyl. Preferably, the aryl group is phenyl or naphthyl.

The term "arylalkyl" includes groups such as benzyl and phenethyl groups which comprise an alkyl chain with an aryl substituent.

The term "heterocyclyl" includes monocyclic, polycyclic, fused or conjugated hydrocarbon residues, preferably $C_{3-6}$, wherein one or more carbon atoms (and where appropriate, hydrogen atoms attached thereto) are replaced by a heteroatom so as to provide a non-aromatic residue. Suitable heteroatoms include O, N, and S. When two or more carbon atoms are replaced, this may be by two or more of the same heteroatom or by different heteroatoms. Suitable examples of heterocyclic groups include pyrollodinyl, piperidyl, piperazinyl, morpholino, quinolinyl, isoquinolinyl, thiomorpholino, dioxanyl, tetrahydrofuranyl, tetrahydropyranyl, and tetrahydropyrrolyl.

The term "heteroaryl" includes a 5- or 6-membered heteroaromatic ring containing one or more heteroatoms selected from O, N and S. Suitable examples of heteroaryl groups include tetrazolyl, 1,2,3-triazolyl, 1,2,4-triazolyl, imidazolyl, pyrazolyl, pyridinyl, pyrimidinyl, oxazolyl, and oxadiazolyl.

Each alkyl, cycloalkyl, alkoxy, oxoalkyl, alkenyl, heterocyclyl, heteroaryl, aryl, and arylalkyl group may optionally be substituted by one or more groups selected from alkyl, cycloalkyl, alkenyl, alkynyl, aryl, arylalkyl, heterocyclyl, heteroaryl, cyano, halo, carboxyl, haloalkyl, haloalkynyl, hydroxy, substituted or unsubstituted alkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocyclyl, heterocycloxy, heterocyclamino, haloheterocyclyl, alkylsulfenyl, alkylcarbonyloxy, alkylthio, acylthio, phosphorus-containing groups such as phosphono and phosphinyl.

In order that the nature of the present invention may be more clearly understood, preferred forms thereof will now be described with reference to the following non-limiting examples.

General Procedures

Mono-Coupling Palladium-Catalysed Cross-Coupling Reaction.

Procedure Utilising Potassium Fluoride as Base and Toluene/Water Solvent Mixture at Reflux:

A mixture containing 4-bromo-5(H)furanone (1 mmol), phenylboronic acid (1.2 mmol), trans-dichlorobis(triphenylphosphine)palladium (II) (0.05 mmol), tetrabutylammonium iodide (0.05 mmol) and potassium fluoride (6 mmol) in toluene (10 mL) and water (10 mL) were gently refluxed for 12-24 h under nitrogen before the reaction mixture was allowed to cool to room temperature. Brine (50 mL) was added and the product extracted with ethyl acetate (3×50 mL). The organic fractions were combined, washed with brine (3×50 mL), dried over anhydrous magnesium sulfate and evaporated to dryness under reduced pressure. The resulting solid was chromatographed (silica gel: eluent 25:75 dichloromethane/light petroleum, 50:50 dichloromethane/light petroleum or 100% dichloromethane) giving the desired product 4-phenyl-5(H)furanone.

Procedure Utilising Potassium Fluoride as Base and Tetrahydrofuran/Water Solvent Mixture at Reflux:

A mixture containing 4-bromo-5(H)furanone (1 mmol), phenylboronic acid (1.2 mmol), trans-dichlorobis(triphenylphosphine)palladium (II) (0.05 mmol), tetrabutylammonium iodide (0.05 mmol) and aqueous potassium fluoride (2M, 6 mmol) in tetrahydrofuran (15 mL) was refluxed for 12-24 h under nitrogen before the reaction mixture was allowed to cool to room temperature. Brine (50 mL) was added and the product extracted with ethyl acetate (3×50 mL). The organic fractions were combined, washed with brine (3×50 mL), dried over anhydrous magnesium sulfate and evaporated to dryness under reduced pressure. The resulting solid was chromatographed (silica gel: eluent 25:75 dichloromethane/light petroleum, 50:50 dichloromethane/light petroleum or 100% dichloromethane) giving the desired product—4-phenyl-5(H)furanone.

Procedure Utilising Potassium Fluoride as Base and Tetrahydrofuran/Water Solvent Mixture at Room Temperature:

A mixture containing 4-bromo-5(H)furanone (1 mmol), phenylboronic acid (1.2 mmol), trans-dichlorobis(triphenylphosphine)palladium (II) (0.05 mmol), tetrabutylammonium iodide (0.05 mmol) and aqueous potassium fluoride (2M, 6 mmol) in tetrahydrofuran (15 mL) was stirred at room temperature for 24-48 h under nitrogen. Brine (50 mL) was added and the product extracted with ethyl acetate (3×50 mL). The organic fractions were combined, washed with brine (3×50 mL), dried over anhydrous magnesium sulfate and evaporated to dryness under reduced pressure. The resulting solid was chromatographed (silica gel: eluent 25:75 dichloromethane/light petroleum, 50:50 dichloromethane/light petroleum or 100% dichloromethane) giving the desired product—4-phenyl-5(H)furanone.

Procedure Utilising Cesium Fluoride as Base and Toluene/Water Solvent Mixture at Room Temperature:

A mixture containing 4-bromo-5(H)furanone (1 mmol), phenylboronic acid (1.2 mmol), trans-dichlorobis(triphenylphosphine)palladium (II) (0.05 mmol), tetrabutylammonium iodide (0.05 mmol) and cesium fluoride (3 mmol) in toluene (10 mL) and water (10 mL) were stirred for 48-72 h under nitrogen at room temperature. Brine (50 mL) was added and the product extracted with ethyl acetate (3×50 mL). The organic fractions were combined, washed with brine (3×50 mL), dried over anhydrous magnesium sulfate and evaporated to dryness under reduced pressure. The resulting solid was chromatographed (silica gel:eluent 25:75 dichloromethane/light petroleum, 50:50 dichloromethane/light petroleum or 100% dichloromethane) giving the desired product—4-phenyl-5(H)furanone.

Procedure Utilising Cesium Fluoride as Base and Toluene/Water Solvent Mixture at Reflux:

A mixture containing 4-bromo-5(H)furanone (1 mmol), phenylboronic acid (1.2 mmol), trans-dichlorobis(triphenylphosphine)palladium (II) (0.05 mmol), tetrabutylammonium iodide (0.05 mmol) and cesium fluoride (3 mmol) in toluene (10 mL) and water (10 mL) were stirred at reflux for 12-24 h under nitrogen. After cooling brine (50 mL) was added and the product extracted with ethyl acetate (3×50 mL). The organic fractions were combined, washed with brine (3×50 mL), dried over anhydrous magnesium sulfate and evaporated to dryness under reduced pressure. The resulting solid was chromatographed (silica gel: eluent 25:75 dichloromethane/light petroleum, 50:50 dichloromethane/light petroleum or 100% dichloromethane) giving the desired product—4-phenyl-5(H)furanone.

Di-Coupling Palladium-Catalysed Cross-Coupling Reaction.
Procedure Utilising Cesium Fluoride as Base and Toluene/Water Solvent Mixture at Room Temperature:

A mixture containing 4-bromo-5-bromomethylene-2(5H)-furanone (1 mmol), phenylboronic acid (2.2 mmol), trans-dichlorobis(triphenylphosphine)palladium (II) (0.05 mmol), tetrabutylammonium iodide (0.05 mmol) and cesium fluoride (3 mmol) in toluene (10 mL) and water (10 mL) were stirred for 48-72 h under nitrogen at room temperature. Brine (50 mL) was added and the product extracted with ethyl acetate (3×50 mL). The organic fractions were combined, washed with brine (3×50 mL), dried over anhydrous magnesium sulfate and evaporated to dryness under reduced pressure. The resulting solid was chromatographed (silica gel: eluent 25:75 dichloromethane/light petroleum, 50:50 dichloromethane/light petroleum or 100% dichloromethane) giving the desired product—4-phenyl-5-bromomethylene-2-(5H)-furanone.

EXAMPLES

1. Compounds

Example 1

4-(2',4'-Difluorophenyl)furan-2(5H)-one 1

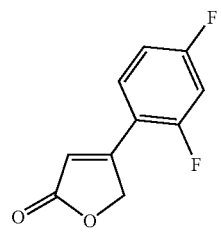

A mixture containing 4-bromo-5(H)furanone (0.211 g, 1.295 mmol), pinacolate(2,4-difluorophenylboronic)ester (0.402 g, 1.675 mmol), trans-dichlorobis(triphenylphosphine)palladium (II) (0.047 g, 6.696×10$^{-2}$ mmol), tetrabutylammonium iodide (0.028 g, 7.580×10$^{-2}$ mmol) and potassium fluoride (0.325 g, 5.594 mmol) in toluene (10 mL) and water (10 mL) were gently refluxed for 24 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a dark brown solid. The resulting solid was chromatographed (silica gel: eluent 50:50 dichloromethane/light petroleum followed by 100% dichloromethane) to give 4-(2',4'-difluorophenyl)furan-2(5H)-one 1 (0.162 g, 64%) as a pale yellow powder, dec. 135-136° C. (ref. PDS-1-59). UV-Vis $\lambda_{max}$ (MeOH) 242(429) nm; $^1$H NMR (CDCl$_3$, 300 MHz) δ 7.48 (ddd, 2H, J=6.0 Hz, J=8.3 Hz, J=14.3 Hz, H6'), 7.05-6.93 (m, 2H, H3', H5'), 6.48 (t, 1H, J=1.5 Hz, H3), 5.24 (t, 2H, J=1.9 Hz, H5); $^{13}$C NMR (CDCl$_3$, 75 MHz) δ 173.4 (C2), 166.4 (d, J=13.0 Hz, C4'), 163.1 (dd, J=12.3 Hz, J=15.2 Hz, C4), 159.8 (d, J=12.3 Hz, C2'), 157.3 (d, J=2.9 Hz, C1'), 129.4 (d, J=5.1 Hz, J=10.1 Hz, C6'), 115.8 (dd, J=2.2 Hz, J=8.7 Hz, C33), 112.9 (dd, J=3.6 Hz, J=21.7 Hz, C5'), 105.4 (t, J=25.3 Hz, C3'), 71.7 (d, J=7.2 Hz, C5); $^{19}$F NMR (CDCl$_3$, 282 MHz) δ −103.27 (d, 1F, J=10.32 Hz, C2'-F), −105.56 (d, 1F, J=10.32 Hz, C4'-F); IR (KBr) 3118, 3076, 3059, 1799, 1739, 1619, 1586, 1509, 1456, 1433, 1358, 1332, 1267, 1167, 1149, 1107, 1051, 997, 961, 898, 889, 874, 811, 735, 619, 584, 528, 453 cm$^{-1}$.

Example 2

4-(4'-Fluorophenyl)furan-2(5H)-one 2

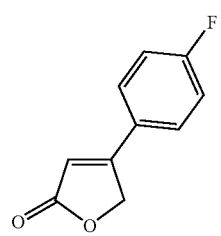

A mixture containing 4-bromo-5(H)furanone (0.249 g, 1.528 mmol), 4-fluorophenylboronic acid (0.280 g, 2.001 mmol), trans-dichlorobis(triphenylphosphine)palladium (II)

(0.056 g, 7.978×10$^{-2}$ mmol), tetrabutylammonium iodide (0.032 g, 8.663×10$^{-2}$ mmol) and potassium fluoride (0.369 g, 6.351 mmol) in toluene (10 mL) and water (10 mL) were gently refluxed for 24 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a dark brown solid. The resulting solid was chromatographed (silica gel: eluent 50:50 dichloromethane/light petroleum followed by 100% dichloromethane) to give 4-(4'-fluorophenyl)furan-2(5H)-one 2 (0.208 g, 76%) as a pale yellow powder, dec. 151-153° C. (ref. PDS-1-61). UV-Vis $\lambda_{max}$ (MeOH) 245(790) nm; $^1$H NMR (CDCl$_3$) δ 7.52 (dddd, 2H, J=3.0 Hz, J=5.3 Hz, J=8.3 Hz, J=10.2 Hz, H2', H6'), 7.17 (dddd, 2H, J=3.0 Hz, J=5.3 Hz, J=8.3 Hz, J=9.8 Hz, H3', H5'), 6.33 (t, 1H, J=1.9 Hz, H3), 5.21 (d, 2H, J=1.5 Hz, H5); $^{13}$C NMR (CDCl$_3$, 75 MHz) 173.6 (C2), 166.2 (C4), 162.6 (C4'), 128.6 (d, J=8.7 Hz, C2', C6'), 125.9 (d, J=3.6 Hz, C1'), 116.5 (d, J=22.4 Hz, C3', C5'), 112.7 (d, J=2.2 Hz, C3), 70.8 (C5); $^{19}$F NMR (CDCl$_3$, 282 MHz) δ −106.98 (s, 1F, C4'-F); IR (KBr) 3116, 3072, 2962, 2943, 1786, 1736, 1623, 1598, 1510, 1474, 1451, 1419, 1352, 1322, 1306, 1279, 1224, 1161, 1101, 1047, 991, 891, 872, 860, 840, 817, 807, 706, 587, 549, 542, 475 cm$^{-1}$.

Example 3

4-(4'-Trifluoromethylphenyl)furan-2(5H)-one 3

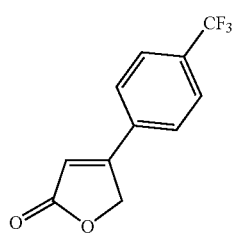

3

Utilization of potassium fluoride as base; A mixture containing 4-bromo-5(H)furanone (0.250 g, 1.534 mmol), pinacolato(4-trifluoromethylphenyl)boronic)ester (0.504 g, 1.852 mmol), trans-dichlorobis(triphenylphosphine)palladium (II) (0.054 g, 7.694×10$^{-2}$ mmol), tetrabutylammonium iodide (0.029 g, 7.851×10$^{-2}$ mmol) and potassium fluoride (0.362 g, 6.231 mmol) in toluene (10 mL) and water (10 mL) were gently refluxed for 24 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a dark brown solid. The resulting solid was chromatographed (silica gel: eluent 50:50 dichloromethane/light petroleum followed by 100% dichloromethane) to give 4-(4'-trifluoromethylphenyl)furan-2(5H)-one 3 (0.206 g, 59%) as a pale yellow powder, dec. 157-158° C. (ref. PDS-1-63). Utilisation of cesium fluoride as base; A mixture containing 4-bromo-5(H)furanone (1.010 g, 6.198 mmol), 4-trifluoromethylphenylboronic acid (1.432 g, 7.540 mmol), trans-dichlorobis(triphenylphosphine)palladium (II) (0.216 g, 3.077×10$^{-1}$ mmol), tetrabutylammonium iodide (0.119 g, 3.222×10$^{-1}$ mmol) and cesium fluoride (4.681 g, 30.811 mmol) in toluene (30 mL) and water (30 mL) were gently refluxed for 24 h under nitrogen before the reaction mixture was allowed to cool to room temperature. Brine (50 mL) was added and the product extracted with ethyl acetate (3×50 mL). The organic fractions were combined, washed with brine (3×50 mL), dried over anhydrous magnesium sulfate and evaporated to dryness under reduced pressure to give a brown solid. The resulting solid was chromatographed (silica gel: eluent 50:50 dichloromethane/light petroleum) to give 4-(4'-trifluoromethylphenyl)furan-2(5H)-one 6 (1.211 g, 86%) as a pale yellow powder, (ref. PDS-2-97). UV-Vis $\lambda_{max}$ (MeOH) 209(16722), 260(20923) nm; $^1$H NMR (CDCl$_3$) δ 7.75 (d, 2H, J=8.3 Hz, H3', H5'), 7.63 (d, 2H, J=8.3 Hz, H2', H6'), 6.48 (t, 1H, J=1.9 Hz, H3), 5.21 (d, 2H, J=1.9 Hz, H5); $^{13}$C NMR (CDCl$_3$, 75 MHz) δ 173.0 (C2), 162.0 (C4), 133.27 (q, J=33.0 Hz, C4'), 132.95 (C1'), 126.8 (C2', C6'), 126.3 (q, J=3.6 Hz, C3', C5'), 123.4 (q, J=270.8 Hz, C4'-CF$_3$), 115.5 (C3), 70.8 (C5); $^{19}$F NMR (CDCl$_3$, 282 MHz) δ −63.54 (s, 3F, C4'-CF$_3$); IR (KBr) 3094, 2941, 1794, 1759, 1626, 1615, 1577, 1439, 1418, 1325, 1247, 1160, 1113, 1070, 1049, 1016, 994, 891, 872, 844, 772, 748, 708, 692, 679, 601, 521, 438, 422 cm$^{-1}$.

Example 4

4-(4'-Cyanophenyl)furan-2(5H)-one 4

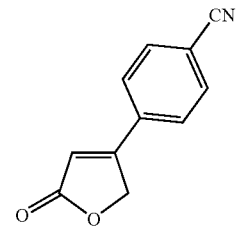

4

A mixture containing 4-bromo-5(H)furanone (0.251 g, 1.540 mmol), 4-cyanophenylboronic acid (0.283 g, 1.887 mmol), trans-dichlorobis(triphenylphosphine)palladium (II) (0.056 g, 7.978×10$^{-2}$ mmol), tetrabutylammonium iodide (0.026 g, 7.040×10$^{-2}$ mmol) and potassium fluoride (0.358 g, 6.162 mmol) in toluene (10 mL) and water (10 mL) were gently refluxed for 24 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a dark brown solid. The resulting solid was chromatographed (silica gel: eluent 50:50 dichloromethane/light petroleum followed by 100% dichloromethane) to give 4-(4'-cyanophenyl)furan-2(5H)-one 4 (0.223 g, 78%) as a pale yellow powder, dec. 227-228° C. (ref. PDS-1-65). Uv-Vis $\lambda_{max}$ (MeOH) 246(1330) nm; $^1$H NMR (CDCl$_3$) δ 7.78 (dd, 2H, J=1.9 Hz, J=6.4 Hz, H2', H6'), 7.61 (dd, 2H, J=2.2 Hz, J=6.4 Hz, H3', H5'), 6.51 (t, 1H, J=1.9 Hz, H3), 5.23 (d, 2H, J=1.9 Hz, H5); $^{13}$C NMR (CDCl$_3$) δ 172.6 (C2), 161.3 (C4), 133.7 (C1'), 133.0 (C3', C5'), 127.0 (C2', C6'), 117.7 (C4'-CN), 116.4 (C3), 115.2 (C4'), 70.7 (C5); IR (KBr) 3098, 2933, 2227, 1790, 1747, 1622, 1605, 1558, 1505, 1450, 1418, 1328, 1279, 1166, 1047, 993, 895, 868, 832, 706, 561, 518 cm$^{-1}$.

Example 5

4-(4'-Trifluoromethoxyphenyl)furan-2(5H)-one 5

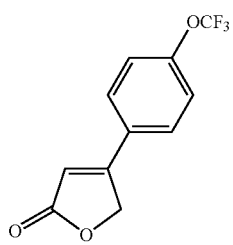 [SMILES: O=C1C=C(c2ccc(OC(F)(F)F)cc2)CO1]

A mixture containing 4-bromo-5(H)furanone (0.274 g, 1.681 mmol), 4-trifluoromethoxyphenylboronic acid (0.417 g, 2.025 mmol), trans-dichlorobis(triphenylphosphine)palladium (II) (0.060 g, 8.548×10$^{-2}$ mmol), tetrabutylammonium iodide (0.032 g, 8.663×10$^{-2}$ mmol) and potassium fluoride (0.401 g, 6.902 mmol) in toluene (10 mL) and water (10 mL) were gently refluxed for 24 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a dark brown solid. The resulting solid was chromatographed (silica gel: eluent 100% dichloromethane) to give 4-(4'-trifluoromethoxyphenyl)furan-2(5H)-one 5 (0.354 g, 86%) as a pale yellow powder, m.p. 122-123° C. (ref. PDS-1-115). UV-Vis $\lambda_{max}$ (MeOH) 211(22865), 269 (28180) nm; $^1$H NMR (CDCl$_3$) δ 7.56 (dt, 2H, J=2.6 Hz, J=9.4 Hz, H2', H6'), 7.32 (d, 2H, J=7.9 Hz, H3', H5'), 6.38 (t, 1H, J=1.9 Hz, H3), 5.21 (d, 2H, J=1.9 Hz, H5); $^{13}$C NMR (CDCl$_3$) δ 173.3 (C2), 162.2 (C4'), 151.4 (C4), 128.20 (C1'), 128.17 (C3), 121.4 (C2', C6'), 120.3 (q, J=257.0 Hz, C4'-O CF$_3$), 113.9 (C3', C5'), 70.8 (C5); $^{19}$F NMR (CDCl$_3$, 282 MHz) δ −58.19 (s, 3F, C4'-OCF$_3$); IR (KBr) 3109, 3073, 3011, 2936, 1790, 1747, 1624, 1588, 1513, 1443, 1422, 1252, 1159, 1046, 1018, 989, 921, 893, 847, 804, 742, 705, 611, 556, 471 cm$^{-1}$.

Example 6

4-(Thiophen-2'-yl)furan-2(5H)-one 6

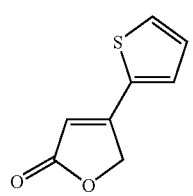

A mixture containing 4-bromo-5(H)furanone (0.271 g, 1.663 mmol), 2-thiopheneboronic acid (0.265 g, 2.071 mmol), trans-dichlorobis(triphenylphosphine)palladium (II) (0.060 g, 8.548×10$^{-2}$ mmol), tetrabutylammonium iodide (0.030 g, 8.122×10$^{-2}$ mmol) and potassium fluoride (0.386 g, 6.644 mmol) in toluene (10 mL) and water (10 mL) were gently refluxed for 12 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a dark brown solid. The resulting solid was chromatographed (silica gel: eluent 50:50 dichloromethane/light petroleum followed by 100% dichloromethane) to give 4-(thiophen-2'-yl)furan-2(5H)-one 6 (0.245 g, 89%) as a pale yellow powder, m.p. 94-96.5° C. (ref. PDS-2-3). UV-Vis $\lambda_{max}$ (MeOH) 246(1870), 349(909) nm; $^1$H NMR (CDCl$_3$) δ 7.50 (d, 1H, J=4.9 Hz, H3'), 7.26 (d, 1H, J=3.4 Hz, H5'), 7.06 (t, 1H, J=4.5 Hz, H4'), 6.03 (s, 1H, H3), 5.07 (d, 2H, J=1.5 Hz, H5); $^{13}$C NMR (CDCl$_3$, 75 MHz) δ 173.2 (C2), 157.1 (C4), 132.3 (C2'), 130.3 (C5'), 128.4 (C4'), 128.2 (C3'), 110.6 (C3), 70.6 (C5); IR (KBr) 3097, 3084, 2934, 1788, 1735, 1616, 1450, 1421, 1354, 1322, 1244, 1204, 1157, 1090, 1033, 892, 872, 858, 840, 822, 730, 704, 638 cm$^{-1}$;

Example 7

4-(3',5'-Dimethylisoxazol-4'-yl)furan-2(5H)-one 7

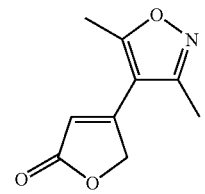

A mixture containing 4-bromo-5(H)furanone (0.288 g, 1.767 mmol), 4-(3,5-dimethylisoxazoleboronic acid (0.299 g, 2.122 mmol), trans-dichlorobis(triphenylphosphine)palladium (II) (0.063 g, 8.976×10$^{-2}$ mmol), tetrabutylammonium iodide (0.031 g, 8.392×10$^{-2}$ mmol) and potassium fluoride (0.338 g, 5.818 mmol) in toluene (10 mL) and water (10 mL) were gently refluxed for 12 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a dark brown solid. The resulting solid was chromatographed (silica gel: eluent 50:50 dichloromethane/light petroleum followed by 100% dichloromethane) to give 4-(3',5'-dimethylisoxazol-4'-yl)furan-2(5H)-one 7 (0.229 g, 72%) as a pale yellow powder, m.p. 101-103° C. (ref. PDS-2-5). UV-Vis $\lambda_{max}$ (MeOH) 246(489) nm; $^1$H NMR (CDCl$_3$, 300 MHz) δ 6.13 (t, 1H, J=1.5 Hz, H3), 5.13 (d J=1.9 Hz, H4), 2.55 (s, 3H, C3'-CH$_3$), 2.38 (s, 3H, C5'-CH$_3$); $^{13}$C NMR (CDCl$_3$, 75 MHz) δ 173.1 (C2), 169.3 (C5'), 158.2 (C4), 154.4 (C3'), 113.2 (C3), 108.0 (C4'), 71.3 (C5), 13.3 (C3'-CH$_3$), 12.0 (C5'-CH$_3$); IR (KBr) 3114, 2974, 2938, 1799, 1763, 1635, 1620, 1591, 1496, 1448, 1425, 1415, 1392, 1352, 1270, 1238, 1160, 1063, 1016, 980, 895, 847, 759, 739, 706, 583, 511 cm$^{-1}$.

Example 8

4-(3'-Trifluoromethylphenyl)furan-2(5H)-one 8

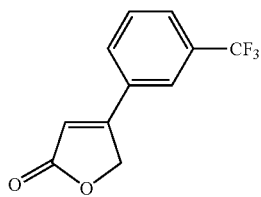 [SMILES: O=C1C=C(c2cccc(C(F)(F)F)c2)CO1]

8

A mixture containing 4-bromo-5(H)furanone (0.280 g, 1.712 mmol), 3-trifluoromethylphenylboronic acid (0.406 g, 2.138 mmol), trans-dichlorobis(triphenylphosphine)palladium (II) (0.061 g, 8.691×10$^{-2}$ mmol), tetrabutylammonium iodide (0.032 g, 8.663×10$^{-2}$ mmol) and potassium fluoride (0.427 g, 7.349 mmol) in toluene (10 mL) and water (10 mL) were gently refluxed for 12 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a dark brown solid. The resulting solid was chromatographed (silica gel: eluent 50:50 dichloromethane/light petroleum followed by 100% dichloromethane) to give 4-(3'-trifluoromethylphenyl)furan-2(5H)-one 8 (0.377 g, 96%) as a pale yellow powder, m.p. 124-125° C. (ref. PDS-2-7). UV-Vis $\lambda_{max}$ (MeOH) 211(17625), 262(17835) nm; $^1$H NMR (CDCl$_3$, 300 MHz) δ 7.76-7.70 (m, 3H, H2', H4', H6'), 7.64 (q, 1H, J=7.5 Hz, H5'), 6.46 (t, 1H, J=1.9 Hz, H3), 5.24 (d, 2H, J=1.9 Hz, H5); $^{13}$C NMR (CDCl$_3$, 75 MHz) δ 173.0 (C2), 162.1 (C4), 131.9 (q, J=33.2 Hz, C3'), 130.5 (C1'), 130.0 (C6'), 129.6 (C5'), 128.1 (q, J=4.3 Hz, C4'), 123.4 (t, J=270.8 Hz, C3'-CF$_3$), 123.1 (q, J=3.6 Hz, C2'), 114.8 (C3), 70.8 (C5); $^{19}$F NMR (CDCl$_3$, 282 MHz) δ -63.40 (s, 3F, C3'-CF$_3$); IR (KBr) 3102, 3077, 2939, 2875, 1943, 1783, 1743, 1627, 1498, 1455, 1437, 1366, 1339, 1317, 1269, 1236, 1160, 1121, 1097, 1077, 1054, 997, 888, 865, 819, 780, 694, 679, 646, 545, 437, 413 cm$^{-1}$.

Example 9

4-(2'-Trifluoromethylphenyl)furan-2(5H)-one 9

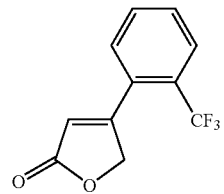

9

A mixture containing 4-bromo-5(H)furanone (0.267 g, 1.638 mmol), 2-trifluoromethylphenylboronic acid (0.382 g, 2.011 mmol), trans-dichlorobis(triphenylphosphine)palladium (II) (0.059 g, 8.406×10$^{-2}$ mmol), tetrabutylammonium iodide (0.041 g, 1.110×10$^{-1}$ mmol) and potassium fluoride (0.380 g, 6.540 mmol) in toluene (10 mL) and water (10 mL) were gently refluxed for 12 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a dark brown solid. The resulting solid was chromatographed (silica gel: eluent 50:50 dichloromethane/light petroleum followed by 100% dichloromethane) to give 4-(2'-trifluoromethylphenyl)furan-2(5H)-one 9 (0.210 g, 56%) as a pale yellow powder, m.p. 49-50° C. (ref. PDS-2-9). UV-Vis $\lambda_{max}$ (MeOH) 208(29654) nm; $^1$H NMR (CDCl$_3$, 300 MHz) δ 7.81 (dd, 1H, J=1.1 Hz, J=7.1 Hz, H3'), 7.68-7.57 (m, 2H, H5', H6'), 7.38 (d, 1H, J=7.2 Hz, H4'), 6.24 (t, 1H, J=1.9 Hz, H3), 5.07 (d, 2H, J=2.3 Hz, H5); $^{13}$C NMR (CDCl$_3$, 75 MHz) δ; $^{19}$F NMR (CDCl$_3$, 282 MHz) δ -58.64 (s, 3F, C2'-CF$_3$); IR (KBr) 3109, 2940, 1786, 1751, 1638, 1602, 1580, 1498, 1447, 1317, 1295, 1269, 1237, 1163, 1126, 1069, 1047, 1036, 996, 887, 872, 775, 756, 731, 707, 669, 641, 595, 548, 522, 496 cm$^{-1}$.

Example 10

4-(Furan-3'-yl)furan-2(5H)-one 10

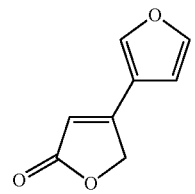

10

A mixture containing 4-bromo-5(H)furanone (0.261 g, 1.602 mmol), pinacolate(3-furanboronic)ester (0.392 g, 2.020 mmol), trans-dichlorobis(triphenylphosphine)palladium (II) (0.058 g, 8.263×10$^{-2}$ mmol), tetrabutylammonium iodide (0.062 g, 1.678×10$^{-1}$ mmol) and potassium fluoride (0.393 g, 6.764 mmol) in toluene (10 mL) and water (10 mL) were gently refluxed for 12 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a dark brown solid. The resulting solid was chromatographed (silica gel: eluent 50:50 dichloromethane/light petroleum followed by 100% dichloromethane) to give 4-(3'-furan)furan-2(5H)-one 10 (0.043 g, 18%) as brown needles, m.p. 101-102° C. (ref. PDS-2-11). UV-Vis $\lambda_{max}$ (MeOH) 244(1724) nm; $^1$H NMR (CDCl$_3$, 300 MHz) δ 7.73 (s, 1H, H2'), 7.53 (t, 1H, J=1.5 Hz, H5'), 6.60 (t, 1H, J=1.1 Hz, H3), 6.11 (t, 1H, J=1.5 Hz, H4'), 5.06 (d, 2H, J=1.9 Hz, H5); $^{13}$C NMR (CDCl$_3$, 75 MHz) δ 173.7 (C2), 156.2 (C4), 145.0 (C4'), 141.9 (C1'), 117.5 (C2'), 112.4 (C3), 108.2 (C3'), 70.8 (C5); IR (KBr) 3141, 3114, 3051, 1790, 1736, 1673, 1519, 1470, 1447, 1405, 1355, 1322, 1275, 1236, 1158, 1019, 894, 871, 852, 828, 752, 702, 644, 596, 547, 527, 501 cm$^{-1}$.

Example 11

4-Bromofuran-2(5H)-one 11

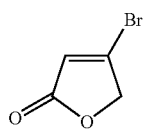

Under and inert atmosphere of anhydrous nitrogen, a solution of oxalyl bromide (10.5 mL, 111.888 mmol) in anhydrous dichloromethane (20 mL) was added dropwise over a 1 h period to a cold (−20° C.) solution of tetronic acid (10.013 g, 100.060 mmol) in a solvent mixture of anhydrous dimethylformamide (10 mL) and anhydrous dichloromethane (200 mL) resulting in the formation of a yellow precipitate. The resulting yellow mixture was allowed to warm slowly over 1 h to 0° C. before the ice bath was removed and the resulting yellow mixture allowed to stir for a further 4 h at room temperature, which during this time the yellow precipitate darkened and turned green. Water (100 mL) was added and the product extracted with diethyl ether (3×200 mL). The organic fractions were combined, washed with water (2×100 mL), saturated sodium bicarbonate (2×200 mL), brine (2×200 mL), dried over anhydrous magnesium sulfate and evaporated to dryness under reduced pressure to give a pale brown coloured solid. The resulting solid was chromatographed (silica gel: eluent 50:50 dichloromethane/light petroleum) to give 4-bromofuran-2(5H)-one 11 (12.578 g, 77%) as a yellow solid. Recrystallisation from diethyl ether gave 4-bromo-5(H)furanone 11 as colourless needles, m.p. 72-74° C. (ref. PDS-2-51). UV-Vis $\lambda_{max}$ (MeOH) 221(13428) nm; $^1$H NMR (CDCl$_3$, 300 MHz) δ 6.36 (t, 1H, J=1.9 Hz, H3), 4.87 (t, 1H, J=1.9 Hz, H5); $^{13}$C NMR (CDCl$_3$, 75 MHz) δ 170.8 (C2), 146.1 (C4), 121.8 (C3), 74.9 (C5); IR (Nujol) 3096, 2923, 2853, 1777, 1742, 1598, 1439, 1411, 1341, 1263, 1152, 1056, 1013, 884, 867, 845, 699 cm$^{-1}$.

Example 12

4-(N-Methylpyrazol-4'-yl)furan-2(5H)-one 12

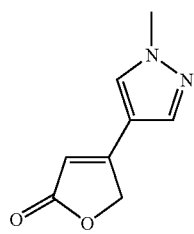

A mixture containing 4-bromo-5(H)furanone (0.247 g, 1.516 mmol), 4-(N-methylpyrazole)boronic acid (0.391 g, 1.879 mmol), trans-dichlorobis(triphenylphosphine)palladium (II) (0.057 g, 8.121×10$^{-2}$ mmol), tetrabutylammonium iodide (0.027 g, 7.310×10$^{-2}$ mmol) and aqueous potassium fluoride (2M, 3 mL, 6.000 mmol) in tetrahydrofuran (17 mL) was refluxed for 12 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a brown solid. The resulting solid was chromatographed (silica gel: eluent 50:50 dichloromethane/light petroleum followed by 100% dichloromethane) to give 4-(N-methylpyrazol-4'-yl)furan-2(5H)-one 12 (0.207 g, 83%) as a pale yellow powder, m.p. 181-182° C. (ref. PDS-2-59). UV-Vis $\lambda_{max}$ (MeOH) 209(2725), 272(4536) nm; $^1$H NMR (CDCl$_3$, 300 MHz) δ 7.69 (s, 1H, H3'), 765 (s, 1H, H5'), 6.03 (t, 1H, J=1.5 Hz, H3), 5.05 (d, 2H, J=1.9 Hz, H5), 3.96 (s, 3H, N1'-CH$_3$); $^{13}$C NMR (CDCl$_3$, 75 MHz) δ 174.2 (C2), 156.5 (C4), 138.1 (C3'), 129.1 (C5'), 113.2 (C4'), 109.8 (C3), 70.9 (C5), 39.4 (N1'-CH$_3$); IR (KBr) 3450, 3174, 3110, 3093, 2949, 1788, 1728, 1636, 1542, 1485, 1441, 1409, 1383, 1347, 1299, 1269, 1261, 1210, 1160, 1065, 1024, 997, 980, 962, 894, 859, 843, 722, 704, 664, 624, 544, 507 cm$^{-1}$.

Example 13

(Z)-4-Phenyl-5-(3'-trifluoromethyl)benzylidene)furan-2(5H)-one 13

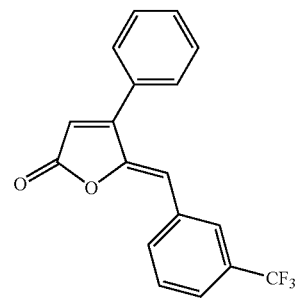

A mixture containing (Z)-5-(bromomethylene)-4-phenyl-furan-2(5H)-one (0.295 g, 1.175 mmol), 3-trifluoromethylphenylboronic acid (0.278 g, 1.464 mmol), trans-dichlorobis(triphenylphosphine)palladium (II) (0.043 g, 6.126×10$^{-2}$ mmol), tetrabutylammonium iodide (0.023 g, 6.227×10$^{-2}$ mmol) and aqueous potassium fluoride (2M, 3 mL, 6.000 mmol) in tetrahydrofuran (17 mL) was refluxed for 24 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a brown solid. The resulting solid was chromatographed (silica gel: eluent 20:80 dichloromethane/light petroleum) to give (Z)-4-phenyl-5-(3'-trifluoromethyl)benzylidene)furan-2(5H)-one 13 (0.337 g, 91%) as a pale yellow powder, m.p. 108-110° C. (ref. PDS-2-65). UV-Vis $\lambda_{max}$ (MeOH) 242(1350), 356(4085) nm; $^1$H NMR (CDCl$_3$, 300 MHz) δ 8.11 (d, 1H, J=7.5 Hz, H4'), 7.91 (s, 1H, H2'), 7.60-7.49 (m, 7H, H2", H3", H4", H5", H5', H6", H6'), 6.27 (s, 1H, H3), 6.19 (s, 1H, H1'''); $^{13}$C NMR (CDCl$_3$, 75 MHz) δ; $^{19}$F NMR (CDCl$_3$, 282 MHz) δ −63.25 (s, 3F, C3'-CF$_3$); IR (KBr) 3067, 1822, 1759, 1650, 1611, 1588, 1573, 1489, 1446, 1350, 1326, 1211, 1188, 1169, 1118, 1072, 1000, 920, 903, 863, 846, 824, 796, 769, 756, 700, 691, 679, 665, 634, 552, 508, 470 cm$^{-1}$.

Example 14

4-(Thiophen-3'-yl)furan-2(5H)-one 14

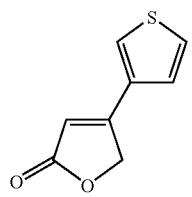 [SMILES: O=C1C=C(c2ccsc2)CO1]

Utilization of potassium fluoride as base in THF; A mixture containing 4-bromo-5(H)furanone (0.252 g, 1.546 mmol), 3-thiopheneboronic acid (0.249 g, 1.946 mmol), trans-dichlorobis(triphenylphosphine)palladium (II) (0.060 g, 8.548×10$^{-2}$ mmol), tetrabutylammonium iodide (0.033 g, 8.934×10$^{-2}$ mmol) and aqueous potassium fluoride (2M, 4 mL, 8.000 mmol) in tetrahydrofuran (16 mL) was stirred at room temperature for 24 h under nitrogen before brine (50 mL) was added and the product extracted with dichloromethane (3×20 mL). The organic fractions were combined, washed with brine (3×20 mL), dried over anhydrous magnesium sulfate and evaporated to dryness under reduced pressure to give a light brown solid. The resulting solid was chromatographed (silica gel: eluent 50:50 dichloromethane/light petroleum followed by 100% dichloromethane) to give 4-(thiophen-3'-yl)furan-2(5H)-one 14 (0.245 g, 95%) as a pale yellow powder. Recrystallisation from dichloromethane/light petroleum furnished colourless needles, m.p. 130.5-132° C. (ref. PDS-2-77). Utilization of cesium fluoride as base in toluene; A mixture containing 4-bromo-5(H)furanone (0.500 g, 3.068 mmol), 3-thiopheneboronic acid (0.710 g, 3.738 mmol), trans-dichlorobis(triphenylphosphine)palladium (II) (0.105 g, 1.496×10$^{-1}$ mmol), tetrabutylammonium iodide (0.068 g, 1.841×10$^{-1}$ mmol) and cesium fluoride (1.951 g, 12.842 mmol) in toluene (10 mL) and water (10 mL) was stirred at reflux for 12 h under nitrogen. The reaction mixture was allowed to cool before brine (50 mL) was added and the product extracted with ethyl acetate (3×50 mL). The organic fractions were combined, washed with brine (3×20 mL), dried over anhydrous magnesium sulfate and evaporated to dryness under reduced pressure to give an orange solid. The resulting solid was chromatographed (silica gel: eluent 50:50 dichloromethane/light petroleum) to give 4-(thiophen-3'-yl)furan-2(5H)-one 18 (0.490 g, 96%) as a yellow powder. Recrystallisation from dichloromethane/light petroleum furnished colourless needles, (ref. PDS-2-113). UV-Vis $\lambda_{max}$ (MeOH) 225(28729), 276(51973) nm; $^1$H NMR (CDCl$_3$, 300 MHz) δ 7.58 (dd, 1H, J=1.5 Hz, J=3.0 Hz, H5'), 7.44 (dd, 1H, J=3.0 Hz, J=5.3 Hz, H4'), 7.28 (dd, 1H, J=1.1 Hz, J=4.9 Hz, H2'), 6.16 (t, 1H, J=1.5 Hz, H3), 5.14 (d, 1H, J=1.9 Hz, H5); $^{13}$C NMR (CDCl$_3$, 75 MHz) δ 174.0 (C2), 158.5 (C4), 131.8 (C3'), 127.6 (C4'), 126.2 (C5'), 125.5 (C3), 111.9 (C2'), 71.0 (C5); IR (KBr) 3119, 3091, 1937, 1793, 1731, 1621, 1506, 1473, 1446, 1423, 1347, 1301, 1199, 1163, 1041, 1003, 928, 894, 870, 842, 798, 791, 714, 700, 634, 619, 545, 488 cm$^{-1}$.

Example 15

4-(2',4'-Bis(trifluoromethyl)phenyl)furan-2(5H)-one 15

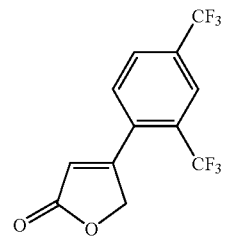

A mixture containing 4-bromo-5(H)furanone (0.331 g, 2.031 mmol), (2',4'-bis(trifluoromethyl)phenyl)boronic acid (0.641 g, 2.485 mmol), trans-dichlorobis(triphenylphosphine)palladium (II) (0.075 g, 1.069×10$^{-1}$ mmol), tetrabutylammonium iodide (0.037 g, 1.002×10$^{-1}$ mmol) and aqueous potassium fluoride (2M, 5 mL, 10.000 mmol) in tetrahydrofuran (15 mL) was refluxed for 48 h under nitrogen before the reaction mixture was allowed to cool to room temperature. Brine (50 mL) was added and the product extracted with dichloromethane (3×20 mL). The organic fractions were combined, washed with brine (3×20 mL), dried over anhydrous magnesium sulfate and evaporated to dryness under reduced pressure to give a brown solid. The resulting solid was chromatographed (silica gel: eluent 50:50 dichloromethane/light petroleum) to give 4-(2',4'-bis(trifluoromethyl)phenyl)furan-2(5H)-one 15 (0.169 g, 28%) as a pale yellow powder. Recrystallisation from dichloromethane/light petroleum furnished colourless needles, m.p. 116-117° C. (ref. PDS-2-81). UV-Vis $\lambda_{max}$ (MeOH) 204(47498) nm; $^1$H NMR (CDCl$_3$, 300 MHz) δ 8.05 (s, 1H, H3'), 7.93 (d, 1H, J=7.9 Hz, H5'), 7.56 (d, 1H, J=7.9 Hz, H6'), 6.30 (t, 1H, J=1.9 Hz, H3), 5.09 (d, 1H, J=2.3 Hz, H5); $^{13}$C NMR (CDCl$_3$, 75 MHz) δ 171.9 (C2), 161.4 (C4), 133.7 (C1'), 132.6 (q, J=33.9 Hz, C4'-CF$_3$), 130.3 (C3), 129.2 (q, J=32.5 Hz, C2'-CF$_3$), 129.1 (d, J=2.9 Hz, C5'), 124.6 (d, J=2.2 Hz, C4'), 124.0 (ddd, J=4.3 Hz, J=7.9 Hz, J=9.4 Hz, C6'), 121.4 (d, J=2.2 Hz, C3'), 121.0 (d, J=2.9 Hz, C2'), 73.3 (d, J=2.2 Hz, C5); $^{19}$F NMR (CDCl$_3$, 470 MHz) δ −59.04 (s, 3F, C2'-CF$_3$), −63.66 (s, 3F, C4'-CF$_3$); IR (KBr) 3138, 3104, 3057, 2938, 1792, 1742, 1649, 1624, 1584, 1510, 1466, 1438, 1353, 1315, 1281, 1269, 1205, 1168, 1144, 1128, 1087, 1068, 1042, 994, 918, 896, 882, 871, 859, 825, 762, 751, 733, 708, 687, 673, 661, 617, 583, 552, 479, 465 cm$^{-1}$.

Example 16

3-Bromo-4-(4'-(trifluoromethyl)phenyl)furan-2-(5H)-one 16

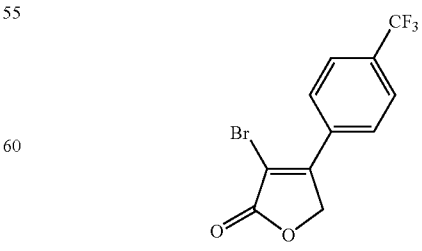

A mixture containing 3,4-dibromofuran-2(5H)-one (0.518 g, 2.142 mmol), 4-trifluoromethylphenylboronic acid (0.509 g, 2.680 mmol), trans-dichlorobis(triphenylphosphine)palladium (II) (0.069 g, 9.831×10$^{-2}$ mmol), tetrabutylammonium iodide (0.038 g, 1.029×10$^{-1}$ mmol) and cesium fluoride (0.872 g, 5.740 mmol) in toluene (10 mL) and water (10 mL) was stirred at room temperature for 72 h under nitrogen. Brine (50 mL) was added and the product extracted with ethyl acetate (3×50 mL). The organic fractions were combined, washed with brine (3×50 mL), dried over anhydrous magnesium sulfate and evaporated to dryness under reduced pressure to give an orange solid. The resulting solid was chromatographed (silica gel: eluent 25:75 dichloromethane/light petroleum) to give 3-bromo-4-(4'-(trifluoromethyl)phenyl) furan-2-(5H)-one 16 (0.312 g, 47%) as a pale yellow powder. Further purification by recrystallisation from dichloromethane/light petroleum furnished colourless needles, (ref. PDS-2-115); $^1$H NMR (CDCl$_3$, 300 MHz) δ 7.94 (d, 2H, J=8.3 Hz, H3', H5'), 7.78 (d, 2H, J=8.3 Hz, H2', H6'), 5.21 (s, 2H, H5).

Example 17

(Z)-4-(4'-(trifluoromethyl)phenyl)-5-(4''-(trifluoromethyl)benzylidene)furan-2(5H)-one 17

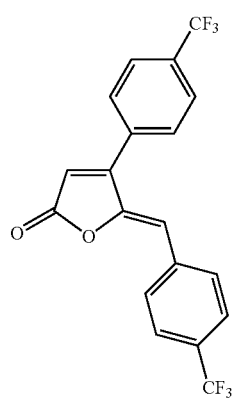

A mixture containing (Z)-5-(bromomethylene)-4-bromo-furan-2(5H)-one (0.505 g, 1.989 mmol), 4-trifluoromethylphenylboronic acid (0.961 g, 5.059 mmol), trans-dichlorobis(triphenylphosphine)palladium (II) (0.070 g, 9.973×10$^{-2}$ mmol), tetrabutylammonium iodide (0.037 g, 1.001×10$^{-1}$ mmol) and cesium fluoride (1.592 g, 10.479 mmol) in toluene (16 mL) and water (16 mL) was stirred at room temperature for 96 h under nitrogen. Brine (50 mL) was added and the product extracted with ethyl acetate (3×20 mL). The organic fractions were combined, washed with brine (3×20 mL), dried over anhydrous magnesium sulfate and evaporated to dryness under reduced pressure to give an orange solid. The resulting solid was chromatographed (silica gel: eluent 25:75 dichloromethane/light petroleum) to give (Z)-4-(4'-(trifluoromethyl)phenyl)-5-(4''-(trifluoromethyl)benzylidene)furan-2(5H)-one 17 (0.581 g, 76%) as a pale yellow powder, m.p. 127.5-129° C. (ref. PDS-2-105). $^1$H NMR (CDCl$_3$, 300 MHz) δ 7.90 (d, 2H, J=8.30 Hz, C3', C5'), 7.82 (d, 2H, J=8.30 Hz, C3'', C5''), 7.65 (d, 2H, J=8.30 Hz, C2', C6'), 7.64 (d, 2H, J=8.30 Hz, C2'', C6''), 6.35 (s, 1H, C3), 6.12 (s, 1H, C1''').

Example 18

(Z)-4-(Thiophen-3-yl)-5-(thiophen-3-ylmethylene) furan-2(5H)-one 18

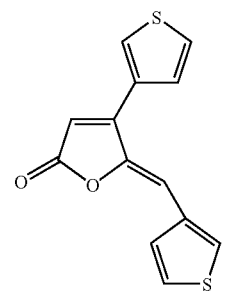

A mixture containing (Z)-4-bromo-5-(bromomethylene) furan-2(5H)-one (0.502 g, 1.977 mmol), 3-thiopheneboronic acid (0.553 g, 4.322 mmol), trans-dichlorobis(triphenylphosphine)palladium (II) (0.068 g, 9.688×10$^{-2}$ mmol), tetrabutylammonium iodide (0.037 g, 1.137×10$^{-1}$ mmol) and cesium fluoride (1.221 g, 8.038 mmol) in toluene (10 mL) and water (10 mL) was stirred at room temperature for 72 h under nitrogen. Brine (50 mL) was added and the product extracted with ethyl acetate (3×50 mL). The organic fractions were combined, washed with brine (3×20 mL), dried over anhydrous magnesium sulfate and evaporated to dryness under reduced pressure to give a dark brown solid. The resulting solid was subjected to recrystallization to give (Z)-4-(thiophen-3-yl)-5-(thiophen-3-ylmethylene)furan-2(5H)-one 18.

Example 19

(Z)-4-(Thiophen-2-yl)-5-(thiophen-2-ylmethylene) furan-2(5H)-one 19

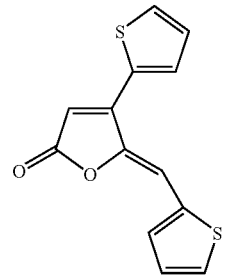

A mixture containing (Z)-4-bromo-5-(bromomethylene) furan-2(5H)-one (0.503 g, 1.981 mmol), 2-thiopheneboronic acid (0.560 g, 4.377 mmol), trans-dichlorobis(triphenylphosphine)palladium (II) (0.072 g, 1.026×10$^{-1}$ mmol), tetrabutylammonium iodide (0.072 g, 1.002×10$^{-1}$ mmol) and cesium fluoride (1.257 g, 8.275 mmol) in toluene (10 mL) and water (10 mL) was stirred at room temperature for 72 h under nitrogen. Brine (50 mL) was added and the product extracted with ethyl acetate (3×50 mL). The organic fractions were combined, washed with brine (3×20 mL), dried over anhydrous magnesium sulfate and evaporated to dryness under reduced pressure to give a dark brown solid. The resulting solid was subjected to recrystallization to give (Z)-4-(thiophen-2-yl)-5-(thiophen-2-ylmethylene)furan-2(5H)-one 19.

Example 20

(Z)-4-(4'-Fluorophenyl)-5-(4"-fluorobenzylidene) furan-2(5H)-one 20

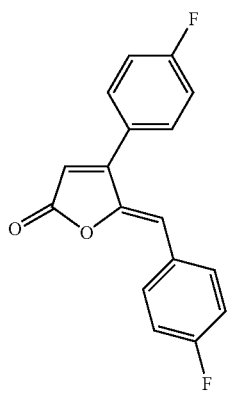

A mixture containing (Z)-4-bromo-5-(bromomethylene) furan-2(5H)-one (0.500 g, 1.969 mmol), 4-fluorophenylboronic acid (0.610 g, 4.360 mmol), trans-dichlorobis(triphenylphosphine)palladium (II) (0.069 g, 9.83×10$^{-2}$ mmol), tetrabutylammonium iodide (0.038 g, 1.029×10$^{-1}$ mmol) and cesium fluoride (1.211 g, 7.972 mmol) in toluene (10 mL) and water (10 mL) was stirred at room temperature for 72 h under nitrogen. Brine (50 mL) was added and the product extracted with ethyl acetate (3×50 mL). The organic fractions were combined, washed with brine (3×20 mL), dried over anhydrous magnesium sulfate and evaporated to dryness under reduced pressure to give a dark brown solid. The resulting solid was subjected to recrystallization to give (Z)-4-(4'-fluorophenyl)-5-(4"-fluorobenzylidene)furan-2(5H)-one 20.

Example 21

(Z)-4-(4'-(Trifluoromethoxy)phenyl)-5-(4"-(trifluoromethoxy)benzylidene)furan-2(5H)-one 21

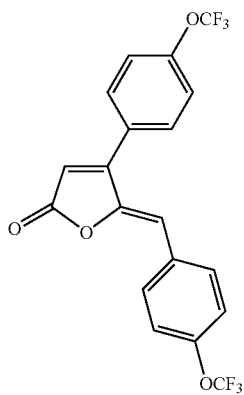

A mixture containing (Z)-4-bromo-5-(bromomethylene) furan-2(5H)-one (0.5026 g, 1.980 mmol), 4-(trifluoromethoxy)phenylboronic acid (0.8983 g, 4.362 mmol), trans-dichlorobis(triphenylphosphine)palladium (II) (0.0711 g, 1.013×10$^{-1}$ mmol), tetrabutylammonium iodide (0.0381 g, 1.031×10$^{-1}$ mmol) and cesium fluoride (1.3094 g, 8.620 mmol) in toluene (10 mL) and water (10 mL) was stirred at room temperature for 72 h under nitrogen. Brine (50 mL) was added and the product extracted with ethyl acetate (3×50 mL). The organic fractions were combined, washed with brine (3×20 mL), dried over anhydrous magnesium sulfate and evaporated to dryness under reduced pressure to give a dark brown solid. The resulting solid was subjected to recrystallization to give (Z)-4-(4'-(trifluoromethoxy)phenyl)-5-(4"-(trifluoromethoxy)benzylidene)furan-2(5H)-one 21.

Example 22

(Z)-4-(4'-Cyanophenyl)-5-(4"-cyanobenzylidene) furan-2(5H)-one 22

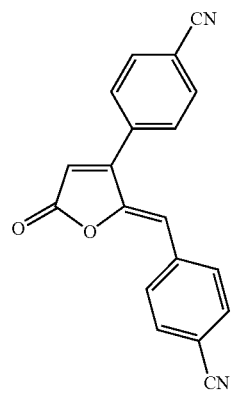

A mixture containing (Z)-4-bromo-5-(bromomethylene) furan-2(5H)-one (0.5315 g, 2.094 mmol), 4-cyanophenylboronic acid (0.6583 g, 4.390 mmol), trans-dichlorobis(triphenylphosphine)palladium (II) (0.0688 g, 9.802×10$^{-2}$ mmol), tetrabutylammonium iodide (0.0366 g, 9.908×10$^{-2}$ mmol) and cesium fluoride (1.2432 g, 8.184 mmol) in toluene (10 mL) and water (10 mL) was stirred at room temperature for 72 h under nitrogen. Brine (50 mL) was added and the product extracted with ethyl acetate (3×50 mL). The organic fractions were combined, washed with brine (3×20 mL), dried over anhydrous magnesium sulfate and evaporated to dryness under reduced pressure to give a dark brown solid. The resulting solid was subjected to recrystallization to give (Z)-4-(4'-cyanophenyl)-5-(4"-cyanobenzylidene)furan-2(5H)-one 22.

Example 23

(Z)-4-(3'-(Trifluoromethyl)phenyl)-5-(3"-(trifluoromethyl)benzylidene)furan-2(5H)-one 23

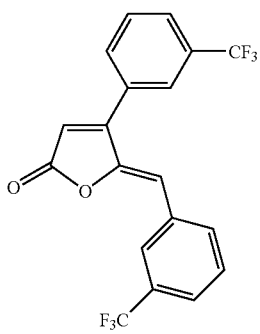

A mixture containing (Z)-4-bromo-5-(bromomethylene) furan-2(5H)-one (0.5038 g, 1.984 mmol), 3-(trifluoromethyl)

phenylboronic acid (0.8330 g, 4.386 mmol), trans-dichlorobis(triphenylphosphine)palladium (II) (0.0746 g, 1.063×10$^{-1}$ mmol), tetrabutylammonium iodide (0.0477 g, 1.291×10$^{-1}$ mmol) and cesium fluoride (1.5039 g, 9.901 mmol) in toluene (10 mL) and water (10 mL) was stirred at room temperature for 72 h under nitrogen. Brine (50 mL) was added and the product extracted with ethyl acetate (3×50 mL). The organic fractions were combined, washed with brine (3×20 mL), dried over anhydrous magnesium sulfate and evaporated to dryness under reduced pressure to give a dark brown solid. The resulting solid was subjected to recrystallization to give (Z)-4-(3'-(trifluoromethyl)phenyl)-5-(3"-(trifluoromethyl)benzylidene)furan-2(5H)-one 23.

Examples 24 to 26

In addition, the following compounds were prepared by similar methodologies to those described above:

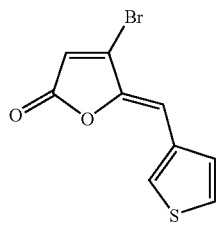 [SMILES: O=C1C=C(Br)/C(=C/c2ccsc2)O1]

24

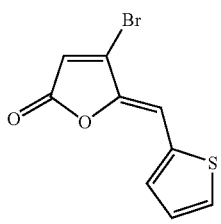 [SMILES: O=C1C=C(Br)/C(=C/c2cccs2)O1]

25

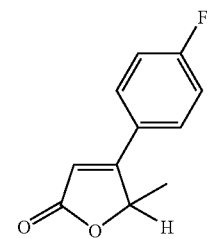

26

Example 27

5-methyl-4-phenyl-2(5H)furanone 27

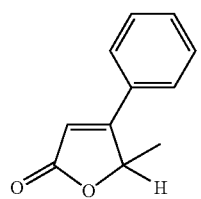

27

A solution of 5-methylene-4-phenyl-2(5H)furanone (2.63 mmol) in ethanol (50 mL) containing Pd—C (25 mgs; 5%) was hydrogenated under an atmosphere of hydrogen at room temperature for 24 hr. The catalyst was filtered off using a pad of Celite and the solvent evaporated in vacuo, leaving a colourless semi-solid, which upon flash chromatography using (EtOAc, CH$_2$Cl$_2$; 1:5) as the eluent gave 5-methyl-4-phenyl-2(5H)furanone 27 as a semi-solid in 90% yield. $^1$H NMR: δ(CDCl$_3$) 3.33 (d, J 4 Hz, 3H, C5-Me), 5.56 (q, J 4 Hz, 1H, C5-H), 6.26 (s, 1H, C3-H) and 7.47 (s, 5H, Ar H's). $^{13}$C NMR: 19.71, 65.85, 66.39, 113.67, 127.11, 129.14, 129.87, 131.20 168.79, 172.54.

Example 28

(Z)-5-(4-fluorobenzylidene)furan-2(5H)-one 28

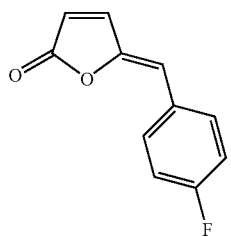

28

A mixture containing 5-bromomethylene-2(5H)furanone (0.175 g, 1 mmol), 4-fluorophenylboronic acid (0.168 g, 1.2 mmol), trans-dichlorobis(triphenylphosphine)palladium (II) (0.035 g, 0.05 mmol), tetrabutylammonium iodide (0.018 g, 0.05 mmol) and cesium fluoride (0.456 g, 3 mmol) in toluene (10 mL) and water (10 mL) were stirred at reflux for 24 hours under nitrogen. After cooling, brine (50 mL) was added and the product extracted with ethyl acetate (50 mL×3). The organic fractions were combined, washed with brine (50 mL×3), dried over anhydrous sodium sulfate and evaporated to dryness to give a brown solid. The resulting solid was chromatographed (silica gel: eluent 50:50 dichloromethane/light petroleum) giving the desired product 28 as a white powder. Yield 0.164 g (86%), m.p. 140-142° C., UV-Vis λ$_{max}$ (MeOH) 225(22535), 330(56424) nm.

$^1$H NMR (CDCl$_3$) δ 7.81-7.74 (m, 2H, H2' and H6'), 7.48 (d, J=5.3 Hz, 1H, H4), 7.11-7.04 (m. 2H, H3' and H5'), 6.20 (d, J=5.3 Hz, 1H, H3), 5.99 (s, 1H, H6). IR (Nujol) 1738, 1600, 1547, 1505, 1462, 1419, 1377, 1304, 1291, 1234, 1185, 1166, 1113, 1094, 1071, 1019, 948, 930, 887, 852, 836, 822, 781, 764 cm$^{-1}$.

Example 29

(Z)-5-(4-(trifluoromethyl)benzylidene)furan-2(5H)-one 29

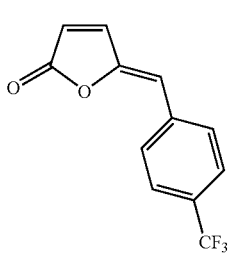

29

A mixture containing 5-bromomethylene-2(5H)furanone (0.175 g, 1 mmol), 4-trifluoromethylphenylboronic acid (0.228 g, 1.2 mmol), trans-dichlorobis(triphenylphosphine) palladium (II) (0.035 g, 0.05 mmol), tetrabutylammonium iodide (0.018 g, 0.05 mmol) and cesium fluoride (0.456 g, 3 mmol) in toluene (10 mL) and water (10 mL) were stirred at reflux for 24 hours under nitrogen. After cooling, brine (50 mL) was added and the product extracted with ethyl acetate (50 mL×3). The organic fractions were combined, washed with brine (50 mL×3), dried over anhydrous sodium sulfate and evaporated to dryness to give a brown solid. The resulting solid was chromatographed (silica gel: eluent 50:50 dichloromethane/light petroleum) giving the desired product 29 as a light yellow powder. Yield 0.133 g (55%), m.p. 92-94° C., UV-Vis $\lambda_{max}$ (MeOH) 223 (15948), 237 (10856), 323(35739) nm. $^1$H NMR (CDCl$_3$) δ 7.87 (d, J=8.3 Hz, 2H, H2' and H6'), 7.63 (d, J=8.3 Hz, 2H, H3' and H5'), 7.52 (d, J=5.7 Hz, 1H, H4), 6.28 (d, J=4.9 Hz, 1H, H3), 6.04 (s, 1H, H6).

$^{13}$C NMR (CDCl$_3$, 75 MHz) δ 169.5 (C), 149.6 (C), 145.0 (CH), 136.1 (C), 130.6 (CH), 130.5 (q, J=32.7 Hz, C), 125.6 (q, J=3.9 Hz, CH), 123.8 (q, J=272.0 Hz, CF$_3$), 119.3 (CH), 112.0 (CH). IR (Nujol) 1784, 1759, 1462, 1376, 1326, 1160, 1111, 1069, 884 cm$^{-1}$.

Example 30

(Z)-5-(3-(trifluoromethyl)benzylidene)furan-2(5H)-one 30

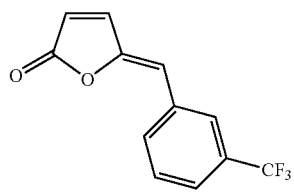

A mixture containing 5-bromomethylene-2(5H)furanone (0.175 g, 1 mmol), 3-trifluoromethylphenylboronic acid (0.228 g, 1.2 mmol), trans-dichlorobis(triphenylphosphine) palladium (II) (0.035 g, 0.05 mmol), tetrabutylammonium iodide (0.018 g, 0.05 mmol) and cesium fluoride (0.456 g, 3 mmol) in toluene (10 mL) and water (10 mL) were stirred at reflux for 24 hours under nitrogen. After cooling, brine (50 mL) was added and the product extracted with ethyl acetate (50 mL×3). The organic fractions were combined, washed with brine (50 mL×3), dried over anhydrous sodium sulfate and evaporated to dryness to give a brown solid. The resulting solid was chromatographed (silica gel: eluent 50:50 dichloromethane/light petroleum) giving the desired product 30 as a light brown powder. Yield 0.180 g (75%), m.p. 69-71° C., UV-Vis $\lambda_{max}$ (MeOH) 223 (15166), 323 (31738) nm.

$^1$H NMR (CDCl$_3$) δ 8.01 (d, J=7.5 Hz, 1H, H6'), 7.92 (s, 1H, H2'), 7.57-7.47 (m, 2H, H4' and H5'), 7.51 (d, J=5.2 Hz, 1H, H4), 6.27-6.25 (m, 1H, H3), 6.03 (s, 1H, H6).

$^{13}$C NMR (CDCl$_3$, 75 MHz) δ 169.5 (C), 149.3 (C), 145.0 (CH), 133.5 (C), 133.4 (CH), 131.2 (q, J=32.4 Hz, C), 129.3 (CH), 127.0 (q, J=3.9 Hz, CH), 125.4 (q, J=3.9 Hz, CH), 123.7 (q, J=272.5 Hz, CF$_3$), 119.1 (CH), 112.0 (CH). IR (Nujol) 1758, 1463, 1326, 1299, 1220, 1165, 1132, 1108, 1097, 1079, 942, 899, 871, 860, 811, 799, 765, 651 cm$^{-1}$.

Example 31

(Z)-5-(Thiophen-3-methylene)furan-2(5H)-one 31

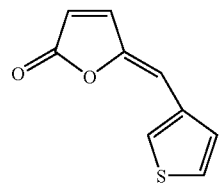

A mixture containing 5-bromomethylene-2(5H)furanone (0.175 g, 1 mmol), 3-thiopheneboronic acid (0.154 g, 1.2 mmol), trans-dichlorobis(triphenylphosphine)palladium (II) (0.035 g, 0.05 mmol), tetrabutylammonium iodide (0.018 g, 0.05 mmol) and cesium fluoride (0.456 g, 3 mmol) in toluene (10 mL) and water (10 mL) were stirred at reflux for 24 hours under nitrogen. After cooling, brine (50 mL) was added and the product extracted with ethyl acetate (50 mL×3). The organic fractions were combined, washed with brine (50 mL×3), dried over anhydrous sodium sulfate and evaporated to dryness to give a brown solid. The resulting solid was chromatographed (silica gel: eluent 50:50 dichloromethane/light petroleum) giving the desired product 31 as a light yellow powder. Yield 0.131 g (74%), m.p. 65-67° C., UV-Vis $\lambda_{max}$ (MeOH) 208 (11976), 239 (8483), 340 (27730) nm. $^1$H NMR (CDCl$_3$) δ 7.76-7.45 (m. 1H, H), 7.54-7.52 (m, 1H, H), 7.46 (d, J=5.3 Hz, 1H, H), 7.36-7.33 (m, 1H, ArH), 6.19-6.17 (m, 1H, H), 6.11 (s, 1H, H6). $^{13}$C NMR (CDCl$_3$, 75 MHz) δ 169.9 (C), 147.4 (C), 144.6 (CH), 134.2 (C), 128.8 (CH), 128.6 (CH), 126.1 (CH), 117.9 (CH), 108.1 (CH). IR (Nujol) 1743, 1645, 1546, 1506, 1463, 1377, 1328, 1243, 1178, 1111, 1074, 964, 934, 890, 879, 793, 766, 708, 646 cm$^{-1}$.

Example 32

(Z)-5-(Thiophen-2-ylmethylene)furan-2-(5H)-one 32

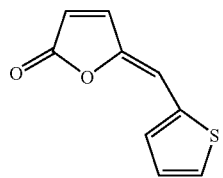

A mixture containing 5-bromomethylene-2(5H)furanone (0.175 g, 1 mmol), 2-thiopheneboronic acid (0.154 g, 1.2 mmol), trans-dichlorobis(triphenylphosphine)palladium (II) (0.035 g, 0.05 mmol), tetrabutylammonium iodide (0.018 g, 0.05 mmol) and cesium fluoride (0.456 g, 3 mmol) in toluene (10 mL) and water (10 mL) were stirred at reflux for 24 hours under nitrogen. After cooling, brine (50 mL) was added and the product extracted with ethyl acetate (50 mL×3). The organic fractions were combined, washed with brine (50 mL×3), dried over anhydrous sodium sulfate and evaporated to dryness to give a brown solid. The resulting solid was chromatographed (silica gel: eluent 50:50 dichloromethane/light petroleum) giving the desired product 32 as a yellow powder. Yield 0.170 g (95%), m.p. 100-102° C. $^1$H NMR (CDCl$_3$) δ 7.50 (d, J=4.9 Hz, 1H, H3'), 7.46 (d, J=5.3 Hz, 1H, H4), 7.38 (d, J=3.4 Hz, 1H, H5'), 7.08-7.05 (m, 1H, H4'), 6.31 (s, 1H, H6), 6.17 (d, J=5.3 Hz, 1H, H3). $^{13}$C NMR (CDCl$_3$, 75 MHz) δ 169.5 (C), 146.6 (C), 143.8 (CH), 136.0 (C), 131.3 (CH), 130.7 (CH), 127.7 (CH), 118.0 (CH), 107.5 (CH). IR (Nujol) 1777, 1738, 1459, 1417, 1376, 1107, 935, 886, 731 cm$^{-1}$.

Example 33

(Z)-5-(4-Methoxybenzylidene)furan-2-(5H)-one 33

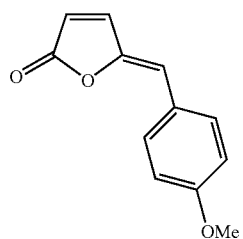

33

A mixture containing 5-bromomethylene-2(5H) furanone (0.175 g, 1 mmol), 4-methoxyphenylboronic acid (0.182 g, 1.2 mmol), trans-dichlorobis(triphenylphosphine)palladium (II) (0.035 g, 0.05 mmol), tetrabutylammonium iodide (0.018 g, 0.05 mmol) and cesium fluoride (0.456 g, 3 mmol) in toluene (10 mL) and water (10 mL) were stirred at reflux for 24 hours under nitrogen. After cooling, brine (50 mL) was added and the product extracted with ethyl acetate (50 mL×3). The organic fractions were combined, washed with brine (50 mL×3), dried over anhydrous sodium sulfate and evaporated to dryness to give a brown solid. The resulting solid was chromatographed (silica gel: eluent 50:50 dichloromethane/light petroleum) giving the desired product 33 as a yellow powder. Yield 0.163 g (80%), m.p. 118-120° C., $^1$H NMR (CDCl$_3$) δ 7.76-7.71 (m, 2H, H3' and H5'), 7.45 (d, J=5.2 Hz, 1H, H4), 6.93-6.88 (m, 2H, H2' and H6'), 6.14-6.12 (m, 1H, H3), 5.97 (bs, 1H, H6), 3.83 (s, 3H). $^{13}$C NMR (CDCl$_3$, 75 MHz) δ 170.5 (C), 160.5 (C), 147.0 (C), 145.0 (C), 132.4 (CH), 125.6 (CH), 116.8 (CH), 114.3 (CH), 114.2 (CH), 55.3 CH$_3$). IR (Nujol) 1789, 1737, 1604, 1551, 1509, 1458, 1376, 1302, 1258, 1175, 1119, 1025, 931, 893, 813 cm$^{-1}$.

Example 34

4-Aryl-1H-pyrrol-2(5H)-ones

Initially a mixture of acetophenone (0.052 mol) and ethylbromoacetate (0.055 mol) was prepared in dry hexane-toluene mixture (50 mls, 1:1; v:v), 10 mL of this solution was added drop wise to pre-heated (ca 40-50° C.) zinc dust (0.055 mol) and the reaction mixture was stirred. After the reaction has commenced, the rest of the solution was added at such a rate so as to maintain a gentle reflux (ca 0.5 hr). After addition, the mixture was heated at reflux for further 2 hr. The mixture was cooled, and sulfuric acid (40 mL; 2.5M) was added to decompose the organo-zinc complex. The organic phase was separated, washed with brine (ca 25 mL), dried (Na$_2$SO$_4$) and the solvent removed in vacuo leaving ethyl-3-aryl-3-hydroxybutanoate as an oil (ca 80-100%), which was used without further purification.

This product was dehydrated by refluxing it with P$_2$O$_5$ (0.052 mol) for 1 hr in toluene (100 mL). The mixture was cooled and passed through a plug of Celite/silica. The solvent was removed, and the residue flash-chromatographed using dichloromethane as eluent giving ethyl-3-aryl-2-butenoate in 80-98% yield. The unsaturated ester, N-bromosuccinimide (1.1 mol/mol) in carbon tetrachloride (100-140 mL) and a few crystals of perbenzoic acid, were heated at reflux for 48 hrs, while shining a 100 watt lamp over the reaction mixture. The mixture was cooled, filtered through a Celite/silica plug, and the solvent evaporated in vacuo leaving ethyl-4-bromo-3-aryl-2-butenoate (60-100%) as a solid/semi-solid. The later product was dissolved in diethylether (ca 40-50 mL) and cooled in a bath of dry ice/acetone. Gaseous ammonia was passed through the mixture till the total volume in the flask reached 100 mL. The mixture was left to warm up to room temperature (4-24 hrs) and the precipitated product was filtered, washed with water, cold ether and dried to yield 4-aryl-1H-pyrrol-2(5H)-one in 30-55% yield.

Example 35

4-(4'-Bromophenyl)-pyrrol-2(5H)-one 35

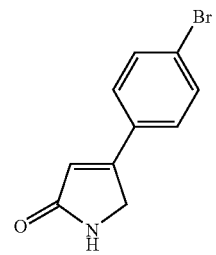

35

4-(4'-Bromophenyl)-pyrrol-2(5H)-one 35 (46%); colourless needles from ethanol, m.p. 233-235° C. (decomp). λ$_{max}$ 218(ε 15,571), 225(14,597) and 278 (26,113) nm. $^1$H N.M.R. δ (DMSO-d$_6$) 4.33 (2H, s, C5-CH$_2$), 6.53 (1H, s, C3-H) and 7.59-7.61 (4H. Ar H's). $^{13}$C N.M.R. δ (DMSO-d$_6$): 22.12, 47.85, 60.62, 72.62, 121.55, 124.38, 123.60, 131.70, 156.18 and 173.80.

Example 36

4-(4'-Fluorophenyl)-1H-pyrrol-2(5H)one 36

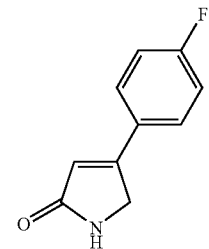

36

4-(4'-Fluorophenyl)-1H-pyrrol-2(5H)one 36, (40%), pale brown needles (ethanol), m.p. 190° C. λ$_{max}$ 205(ε 15,539) and 269 (19,650) nm. $^1$H NMR: δ (CD$_3$OD) 4.47 (2H, s, C5-CH$_2$); 6.41 (s, 1H, C4-H), 7.13-7.19 (t, 2H, Ar H's) and 7.65-7.69 (m, 2H, Ar H's). $^{13}$C NMR: 48.34, 65.38, 115.34, 123.58, 125.23, 125.32, 128.02, 157.88, 165.48 and 175.72.

2. Antibacterial Assays

Example 1

N-Acylated Homoserine Lactone (AHL) Quorum Sensing Assay

The present applicant has demonstrated that certain furanones and furanone analogues can inhibit AHL-mediated quorum sensing in bacteria. Compounds of the present invention were compared to compounds of the prior art in order using an AHL-quorum sensing assay which utilises a reporter strain that expresses Green Fluorescent Protein (GFP) in the presence of AHL signals. The assay is performed by measuring GFP output in the presence of the compound to be measured and comparing the output to a control. By using multiple samples at varying concentrations of compound and AHL, an inhibition index of compound activity can be generated. The inhibition index used in the present example is the relative amount of compound required to reduce GFP expression to 40% of the control. The inhibition index is termed AIC40. Lower values of AIC40 represent better inhibitors of the AHL quorum sensing system.

The reporter strain of bacterium used in this assay is *E. coli* into which the *V. fischeri* luxRI system has been engineered. A gfp gene is fused to the QS controlled luxI promoter as is described in (Andersen et al., 2001, and Andersen et al, 1998).

Measurement of AIC40 (ID40 at 3 nM OHHL)

Determination of the activity of compounds using the *E. coli* based luxRI construct was performed as follows.

Inhibition Kinetics

In a 15 mL plastic tube, mix 3 mL of o.n. culture of the lux reporter strain with 12 mL fresh medium, incubate at 37° C. Label six tubes, 10, 20, two 50 and two 100. To each of the tubes, add OHHL (3-oxohexanoyl homoserine lactone) to a final concentration of 10, 20, 50, or 100 nM respectively in the AB medium (add enough medium to distribute across the appropriate number of wells). To the first row of the microplate (row A), add 200 ul of the OHHL/AB mixture. To the remaining rows (B-H) add 100 ul of the OHHL/AB mixture. To the first row (A) add compounds to be tested to the 200 ul mixture of OHHL/AB. Make a dilution series in the first 7 rows by transferring 100 μL from wells in row 1 to wells in row 2 and so on. Discard the remaining 100 μL from row 7. Add 100 μL diluted lux monitor to each well. Incubate the plate 2 hours at 37° C. and measure green fluorescence using the "Victor" plate reader.

Data Treatment

Calculate $ID_{40}$ for each column. To do this, calculate the relative activity in each well. Each column is calculated separately, the well that does not contain furanone is set to 100% activity (the wells in row 8). Make a plot for each concentration of OHHL vs. the range of compound concentrations used. Calculate the amount of compound needed to lower the relative activity to 40%, this is termed inhibiting dose 40%, $ID_{40}$. For each compound an inhibition index, $AIC_{40}$, is found as follows: plot $ID_{40}$ against its respective AHL concentration; $AIC_{40}$ is the slope of the best straight line through the plotted points and origin.

Compound Measurements

The results of compound measurements using the AHL-quorum sensing assay are shown in Table 1 below.

Example 2

LasR Assay

Compounds of the present invention were also assayed using a LasR assay. The LasR assay provides a measurement of quorum sensing inhibition activity. The higher the percentage inhibition, the more effective the compound. In the LasR assay, an unstable gfp has been fused to the elastase promoter, so that the amount of Gfp is regulated by the QS system. The plasmid is put into *Pseudomonas aeruginosa* which makes its own AHL signals. The assay is performed by adding the compounds to be tested to the system at the beginning of the experiment, at different concentrations. Gfp expression is measured at different times during growth, ending at the 24 h time point. The percentage fluorescence was determined at the time point when the fluorescence reached its maximum in the control, usually around 11-12 h after inoculation.

The results of the compound measurements using the LasR assay are shown in Table 1 below.

TABLE 1

Results of N-acylated homoserine lactone (AHL) quorum sensing assay and LasR assay

| Compound | AIC40 (ID40 at 3 nM OHHL) | LasR (% inhibition at 25 ug/ml compound) |
|---|---|---|
| 2 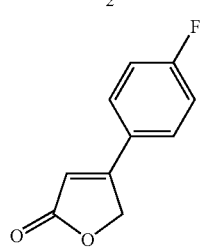 | 14.39 (39.4) | Not tested |

TABLE 1-continued
Results of N-acylated homoserine lactone (AHL) quorum sensing assay and LasR assay
| Compound | AIC40 (ID40 at 3 nM OHHL) | LasR (% inhibition at 25 ug/ml compound) |
|---|---|---|
| 1 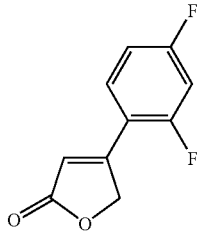 | 7.6 (17.83) | Not tested |
| 3 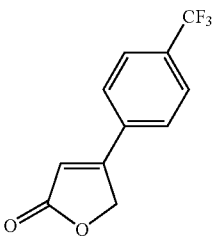 | 0.77 (4.37) | 22% |
| 5 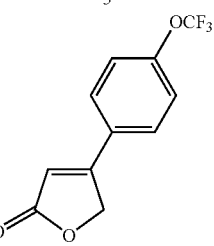 | 5.9 (11.37) | 19.3% (43.2% at 50 μg/ml) |
| 8 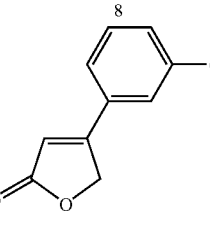 | Not tested | 22% (42.2% at 50 μg/ml) |
| 6 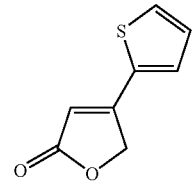 | 24.6 (58.7) | 10% |
| 14 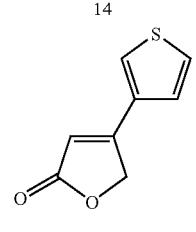 | 4.9 (60 μM) | 15% |

TABLE 1-continued

Results of N-acylated homoserine lactone (AHL) quorum sensing assay and LasR assay

| Compound | AIC40 (ID40 at 3 nM OHHL) | LasR (% inhibition at 25 ug/ml compound) |
|---|---|---|
| 12 | Not tested | (22.9% at 50 μg/ml) |
| 25 | Not tested | 20% (78% at 100 μg/ml) |
| 26 | Not tested | 30% (76% at 100 μg/ml) |
| 27 | Not tested | 9% (57% at 100 μg/ml) |
| 28 | Not tested | 13% (53 at 100 μg/ml) |
| 29 | Not tested | 15.8% 38.4% at 100 μg/ml) |

TABLE 1-continued

Results of N-acylated homoserine lactone (AHL) quorum sensing assay and LasR assay

| Compound | AIC40 (ID40 at 3 nM OHHL) | LasR (% inhibition at 25 ug/ml compound) |
|---|---|---|
| 23 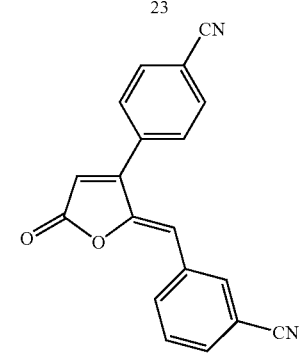 | 4.64 (22.1) | 23% (46.4% at 100 µg/ml) |
| 24 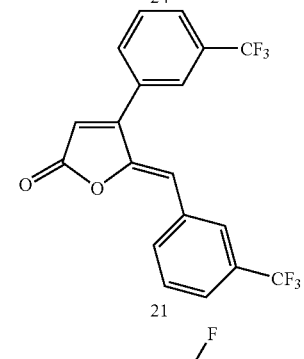 | Not tested | 19% (35% at 100 µg/ml) |
| 21 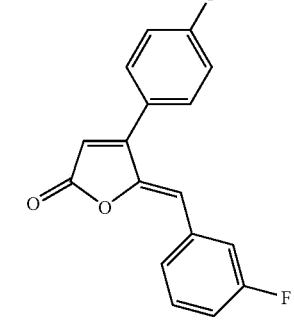 | 4.4 (148) | 14.7% (47% at 100 µg/ml) |

Example 3

Inhibition of Biofilm Formation

Compounds were run in a Petri dish model—where the cells of *E. coli* or *Pseudomonas aeruginosa* were exposed to the compound for 48 h. The amount of biofilm was determined by combining image data of the XY (surface cover in one plane) and XZ (depth). The controls gave good biofilm cover and some structure formation.

| Compound | % biofilm |
|---|---|
| *E. coli* | |
| 6 (40 µg/mL) | 97% |
| 6 (25 µg/mL) | 87.7% |
| *Pseudomonas aeruginosa* | |
| 6 (10 µg/mL) | 77% |

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

ANDERSEN, J. B., HEYDORN, A., HENTZER, M., EBERL, L., GEISENBERGER, O., CHRISTENSEN, B., BAK, MOLIN, S. & GIVSKOV, M. (2001) Gfp-based n-acyl homoserine lactone sensor systems for detection of bacterial communication. *Appl. Environ. Microbiol.*, 67, 575-585.

ANDERSEN, J. B., STERNBERG, C., POULSEN, L. K., BJORN, S. P., GIVSKOV, M. & MOLIN, S. (1998) New unstable variants of green fluorescent protein for studies of transient gene expression in bacteria. *Appl. Environ. Microbiol.*, 64, 2240-2246.

The claims defining the invention are as follows:

1. A compound of formula I

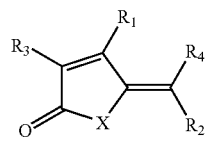

I wherein:

X is —N($R_5$)—;
  wherein $R_5$ is selected from H, alkyl, aryl and arylalkyl;
$R_1$ is phenyl substituted by a substituent selected from the group consisting of $CF_3$, $OCF_3$, cyano and halo;
$R_2$ and $R_4$ are each independently selected from hydrogen and aryl with the proviso that both $R_2$ and $R_4$ cannot be hydrogen; and
$R_3$ is selected from H, alkyl, heteroaryl and aryl.

2. A compound according to claim 1 wherein $R_4$ is H.

3. A compound according to claim 1 wherein $R_3$ is H.

4. A compound according to claim 1 wherein $R_2$ is aryl.

5. A compound according to claim 4 wherein aryl is a phenyl group optionally substituted with one or more substituents selected from the group consisting of $CF_3$, $OCF_3$, cyano, halo, alkoxyl and methoxyl.

6. A compound according to claim 1 wherein aryl is a phenyl group optionally substituted with one or more substituents selected from the group consisting of $CF_3$, $OCF_3$, cyano, halo and.

7. A compound according to claim 1 wherein $R_1$ is phenyl substituted by a substituent selected from the group consisting of $CF_3$, $OCF_3$, cyano, and halo and $R_2$ is aryl.

8. A formulation comprising a compound according to claim 1.

9. A compound according to claim 1 wherein $R_1$ is phenyl substituted by a substituent selected from the group consisting of $CF_3$, $OCF_3$, cyano and F.

10. A compound according to claim 1 wherein X is N; $R_5$ is H; $R_1$ is phenyl with F substituted in the 2-position; $R_2$ is phenyl; $R_3$ is H and $R_4$ is H.

* * * * *